US012753252B2

(12) United States Patent
Wang et al.

(10) Patent No.: US 12,753,252 B2
(45) Date of Patent: Oct. 6, 2026

(54) MONOMER ISOMERIZATION AND POLYMER FLUORINATION FOR SUSTAINABLE DEPOLYMERIZABLE POLYMERS

(71) Applicants: Junpeng Wang, Peninsula, OH (US); Devavrate Sathe, Akron, OH (US); Junfeng Zhou, Shenzhen (CN); Hanlin Chen, Stow, OH (US)

(72) Inventors: Junpeng Wang, Peninsula, OH (US); Devavrate Sathe, Akron, OH (US); Junfeng Zhou, Shenzhen (CN); Hanlin Chen, Stow, OH (US)

(73) Assignee: The University of Akron, Akron, OH (US)

( * ) Notice: Subject to any disclaimer, the term of this patent is extended or adjusted under 35 U.S.C. 154(b) by 764 days.

(21) Appl. No.: 17/937,144

(22) Filed: Sep. 30, 2022

(65) Prior Publication Data

US 2023/0167211 A1 Jun. 1, 2023

Related U.S. Application Data

(60) Provisional application No. 63/334,884, filed on Apr. 26, 2022, provisional application No. 63/284,268, filed on Nov. 30, 2021.

(51) Int. Cl.

| | |
|---|---|
| ***C08F 132/08*** | (2006.01) |
| ***C07C 43/162*** | (2006.01) |
| ***C07C 69/753*** | (2006.01) |
| ***C07D 209/94*** | (2006.01) |

(Continued)

(52) U.S. Cl.

CPC .......... *C08F 132/08* (2013.01); *C07C 43/162* (2013.01); *C07C 69/753* (2013.01); *C07D 209/94* (2013.01); *C07D 307/93* (2013.01); *C08F 299/022* (2013.01)

(58) Field of Classification Search

CPC .. C08F 132/08; C08F 299/022; C07C 43/162; C07C 69/753; C07C 2602/26; C07C 35/23; C07D 209/94; C07D 307/93; C08G 61/08; C08G 2261/3322; C08G 2261/418; Y02W 30/62

See application file for complete search history.

(56) References Cited

PUBLICATIONS

Sathe et al, Olefin metathesis-based chemically recyclable polymers enabled by fused-ring monomers, Nature Chemistry, COI 13, Aug. 2021, 743-750 (Year: 2021).*

* cited by examiner

*Primary Examiner* — Alicia Bland

(74) *Attorney, Agent, or Firm* — Renner, Kenner, Greive, Bobak Taylor & Weber Co., L.P.A.

(57) ABSTRACT

A monomer capable forming a polymer through ring-opening metathesis polymerization and capable of depolymerization thereafter through ring-closing metathesis, wherein the monomer comprises a cycloalkene having a fused ring attached thereto to form a cycloalkene-fused ring monomer, wherein the fused ring decreases the ring strain energy of the cycloalkene to a lower ring strain energy state of 5.3 kcal/mol or lower as compared to the same cycloalkene without the fused ring having a ring strain energy above 5.3 kcal/mol and wherein the cycloalkene-fused ring monomer is capable of isomerization into a higher ring strain energy state before polymerization and method of synthesizing the (Continued)

monomer. The monomer is further capable of forming chemically recyclable to monomers block copolymers.

8 Claims, 4 Drawing Sheets

(51) Int. Cl.
*C07D 307/93* (2006.01)
*C08F 299/02* (2006.01)

| | 3-membered | 4-membered | 5-membered | 6-membered |
|---|---|---|---|---|
| *Cis* |  9.8 kcal mol$^{-1}$ |  10.3 kcal mol$^{-1}$ |  7.6 kcal mol$^{-1}$ |  7.2 kcal mol$^{-1}$ |
| *Trans* |  10.3 kcal mol$^{-1}$ |  4.9 kcal mol$^{-1}$ |  5.3 kcal mol$^{-1}$ |  7.5 kcal mol$^{-1}$ |

Non-substituted

*Trans*-CB

*Cis*-CB

Cyclooctenes 1,9-dienes

MONOMER ISOMERIZATION AND POLYMER FLUORINATION FOR SUSTAINABLE DEPOLYMERIZABLE POLYMERS

CROSS-REFERENCE TO RELATED APPLICATIONS

This application claims the benefit of U.S. Provisional Patent Application Serial Number U.S. 63/284,268 filed Nov. 30, 2021, and U.S. Provisional Patent Application Serial Number U.S. 63/334,884 filed Apr. 26, 2022, both of which are incorporated herein by reference in their entirety.

STATEMENT REGARDING FEDERALLY SPONSORED RESEARCH OR DEVELOPMENT

This invention was made with government support under DMR 2042494 awarded by National Science Foundation. The government has certain rights in the invention.

FIELD OF THE INVENTION

In particular embodiments, the invention relates to modification of cycloalkenes that polymerize through ring-opening metathesis polymerization, the modification providing a fused ring that decreases the ring strain energy (RSE) to an amount suitable for convenient depolymerization. In some embodiments, the cycloalkenes are further modified through cis-to-trans alkene isomerization of the cycloalkene to increase ring strain energy to promote living ring-opening metathesis polymerization, even at reduced monomer concentrations. In some embodiments, the fused ring includes functionalization, and, in some particular embodiments, fluorine functionalization to yield chemically recyclable semi-fluorinated polymers that can be efficiently depolymerized under mild conditions and provide improved thermomechanical properties, hydrophobicity, and maintain chemical recycling to monomers (CRM).

BACKGROUND OF THE INVENTION

Synthetic polymers, including synthetic rubber and synthetic plastics, have been used in nearly every aspect of our daily lives. The dominance of synthetic polymers is largely driven by their excellent stability and processability as well as their versatile mechanical properties. However, due to their high durability, waste materials composed of these polymers have accumulated in the ocean and have caused serious concerns for marine ecosystems. In addition, because 90% of these polymers are derived from finite fossil feedstocks, the production of these materials is unsustainable if they cannot be recycled and reused. Efforts to address these issues include the development of biodegradable polymers and mechanical recycling. However, most biodegradable polymers that can be degraded in artificial environments do not undergo efficient degradation in seawater, giving rise to new environmental consequences. Mechanical recycling of polymers typically results in substantial loss of quality, and the recycled material is not suitable for high-performance applications.

Thus, there is a need for chemically recyclable polymers that can depolymerize into their constituent monomers for recycling and repolymerization. Circular use of the materials not only will help to preserve finite natural resources but also can address end-of-life issues for such materials.

To replace currently available commercial polymers, depolymerizable polymers need to match or exceed the properties of the current ones. With exceptions, polymerization is typically favored in enthalpy ($\Delta H<0$) and disfavored in entropy ($\Delta S<0$). The temperature at which the entropic loss will offset the enthalpic gain is defined as the ceiling temperature $T_c$, and depolymerization is favored when the temperature is above $T_c$. Common polymers such as polyolefins have high $T_c$ values, and their depolymerization is either costly in terms of energy or is susceptible to decomposition. Classical low-$T_c$ polymers such as poly (olefin sulfones), poly($\alpha$-methyl styrene), and polyaldehydes lack high thermal and chemical stability, and their use has been limited to certain specific applications such as transient electronics.

A promising strategy to address the stability issues is to develop polymers that only undergo efficient depolymerization in the presence of a catalyst. In other words, without the catalyst, the polymer is in a kinetic trap so that it will stay intact even when the temperature is above $T_c$. Recently, it has been shown that ring-opening polymerization of certain cyclic monomers—such as cyclic esters, cyclic carbonates, and cyclic olefins—can lead to polymers that can depolymerize into the corresponding monomers in the presence of catalysts but show high thermal stability when the catalysts are removed. For example, Chen and coworkers, Zhu, J.-B., Watson, E. M., Tang, J. & Chen, E. Y. X. A synthetic polymer system with repeatable chemical recyclability, *Science* 360, 398-403 (2018), have shown that a poly($\gamma$-butyrolactone) required heating overnight at 300° C. to be depolymerized, but the depolymerization temperature was reduced to 120° C. when a $ZnCl_2$ catalyst was added.

Among catalytically depolymerizable polymers, ones that are formed through olefin metathesis are particularly attractive since olefin metathesis does not occur without a catalyst, and unintended depolymerization can thus be prevented by removing the catalyst. In addition, metathesis is compatible with a wide variety of functional groups and can be conducted in mild or ambient reaction conditions. Metathesis-based depolymerizable polymers are typically made via ring-opening metathesis polymerization (ROMP) of cycloalkenes and can depolymerize through ring-closing metathesis (RCM) to form the corresponding monomers. Compared to the ring-opening polymerization that is based on cyclic esters and cyclic carbonates, ROMP enables the production of polymers with hydrocarbon backbones, which have greater hydrolytic and thermal stability.

Depolymerizable ROMP polymers have been largely limited to those of the five-membered cyclic olefins, such as cyclopentene and 2,3-dihydrofuran.

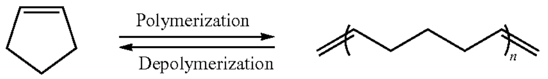

However, living ROMP of the five-membered cyclic olefins is challenging due to their low ring strain. On the other hand, the living ROMP of high-strain monomers, such as norbornene, 7-oxanorbornene, cyclopropene, cyclobutene and trans-cyclooctene have been demonstrated, but they do not depolymerize.

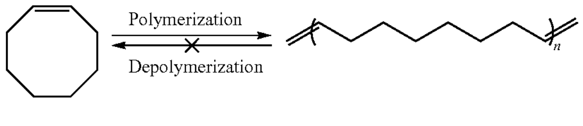

For an efficient living ROMP, the high strain is essential as it favors the propagation over secondary metathesis that causes undesirable chain transfer. It is therefore challenging, if not impossible, to realize both living ROMP and depolymerization of the resulting polymer, as the polymer is not readily broken down to its high-strain monomers.

Thus, there exists a need for chemically recyclable monomers that can undergo depolymerization under mild conditions.

Since the invention of polychlorotrifluoroethylene and polytetrafluoroethylene in the 1930s, fluorinated polymers have come to hold a position of importance in functional materials. The high strength and low polarizability of the C—F bond along with its intrinsic tendency to form weaker van der Waals interactions impart fluorinated polymers with unique and valuable properties, including high hydrophobicity and a low coefficient of friction, as well as solvent, thermal, and chemical resistance. Benefited from these useful properties, fluorinated polymers have become indispensable in a diverse range of applications, including hydrophobic materials, parts for use in chemically harsh conditions, anti-fouling and low-friction surfaces, dielectrics, and separation membranes. The hydrophobicity of fluorinated polymers and their incompatibility with non-fluorinated polymers have also attracted significant interests in the field of self-assembly.

The high-volume production and use of fluorinated polymers needs to be supported by effective recycling to achieve sustainable utilization of natural resources and to reduce environmental impact. At present, most post-consumer fluorinated and semi-fluorinated polymer waste ends up in landfills. This has raised environmental concerns since accumulation of fluorinated polymer waste can lead to the release of highly persistent microplastics that can become a part of the food chain. Current effort in recycling of fluorinated polymers has been focused on mechanical recycling, which requires extensive sorting and the addition of harsh chemicals, and the mechanical processing of the refined material typically leads to the reduction in molecular weight and the deterioration in mechanical properties.

Thus, a need exists to provide a closed-loop life cycle for fluorinated polymers through chemical recycling to monomers (CRM). While polytetrafluoroethylene can depolymerize to form its monomer through pyrolysis; however, its pyrolytic depolymerization results in a mixture of tetrafluoroethene and other fluorinated small molecules, and the process requires high temperatures (>650° C.) and thus large energy inputs. In addition, the pyrolytic depolymerization method is not applicable across a wide range of fluorinated and semi-fluorinated materials. It is therefore desirable to develop fluorinated or semi-fluorinated polymers that can be depolymerized under mild conditions while maintaining their high thermal stability.

SUMMARY OF THE INVENTION

An embodiment of the present invention provides a monomer capable of forming a polymer through ring-opening metathesis polymerization, the polymer being capable of depolymerization thereafter through ring-closing metathesis, the monomer comprising: a cycloalkene having a fused ring attached thereto to form a cycloalkene-fused ring monomer, wherein the fused ring decreases the ring strain energy of the cycloalkene to a lower ring strain energy state of 5.3 kcal/mol or lower as compared to the same cycloalkene without the fused ring having a ring strain energy above 5.3 kcal/mol, and wherein the cycloalkene of the cycloalkene-fused ring monomer is capable of isomerization into a higher ring strain energy state before polymerization.

Another embodiment of the present invention provides a monomer as in any embodiment above, wherein the fused ring is either cis-fused or trans-fused.

Another embodiment of the present invention provides a monomer as in any embodiment above, wherein the cycloalkene is an 8-membered cycloalkene, cyclooctene.

Another embodiment of the present invention provides a monomer as in any embodiment above, wherein the fused ring is a 3- to 6-membered ring.

Another embodiment of the present invention provides a monomer as in any embodiment above, wherein the fused ring is a 4-membered ring, cyclobutane.

Another embodiment of the present invention provides a monomer as in any embodiment above, wherein the fused ring is a 5-membered ring, cyclopentane.

Another embodiment of the present invention provides a monomer as in any embodiment above, wherein the fused ring is fused at the C5, C6-positions of the cyclooctene.

Another embodiment of the present invention provides a monomer as in any embodiment above, wherein the fused ring is trans-cyclobutane or trans-cyclopentane.

Another embodiment of the present invention provides a monomer as in any embodiment above, the fused ring is functionalized after the cycloalkene-fused ring monomer is formed.

Another embodiment of the present invention provides a polymer formed from a monomer as in any embodiment above, wherein a depolymerization product of the polymer is the cycloalkene-fused ring monomer in a lower ring strain energy state.

Another embodiment of the present invention provides a polymer formed from a monomer as in any embodiment above, wherein a functionality of the fused ring is maintained in polymer.

Another embodiment of the present invention provides a polymer formed from a monomer as in any embodiment above, wherein the fused ring is capable of post-polymerization functionalization.

Another embodiment of the present invention provides a block copolymer comprising a first polymer block comprising a plurality of a monomer as in any embodiment above, and further comprising a second polymer block covalently linked to the first polymer block.

An embodiment of the present invention provides a method of forming a chemically recyclable to monomers polymer comprising providing a plurality of monomers comprising a cycloalkene having a fused ring attached thereto to form a cycloalkene-fused ring monomer, wherein the fused ring decreases the ring strain energy of the cycloalkene to a lower ring strain energy state of 5.3 kcal/mol or lower as compared to the same cycloalkene without the fused ring having a ring strain energy above 5.3 kcal/mol and wherein the cycloalkene of the cycloalkene-fused ring monomer is capable of isomerization into a higher ring strain energy state before polymerization, and performing ring-opening metathesis polymerization using at least the plurality of monomers, a catalyst as an initiator, a weakly coordinating ligand, and a coordinating solvent to thereby form the chemically recyclable to monomers, polymer.

Another embodiment of the present invention provides a method of forming a chemically recyclable to monomers polymer as in any embodiment above, wherein an initial concentration of the plurality of monomers is at least 0.010 M.

Another embodiment of the present invention provides a method of forming a chemically recyclable to monomers polymer as in any embodiment above, wherein the catalyst as an initiator comprises a ruthenium-based catalyst.

Another embodiment of the present invention provides a method of forming a chemically recyclable to monomers polymer as in any embodiment above, wherein the weakly coordinating ligand comprises triphenylphosphine, $PPh_3$.

Another embodiment of the present invention provides a method of forming a chemically recyclable to monomers polymer as in any embodiment above, wherein the coordinating solvent comprises tetrahydroguran.

Another embodiment of the present invention provides a method of forming a chemically recyclable to monomers polymer as in any embodiment above, further comprising synthesizing a recyclable block copolymer wherein synthesizing the recyclable block copolymer includes isomerizing the cycloalkene-fused ring monomer prior to performing ring-opening metathesis polymerization, forming a first polymer block comprising the chemically recyclable to monomers, polymer, and forming a second polymer block covalently linked to the first polymer block to thereby form the recyclable block copolymer.

Another embodiment of the present invention provides a method of forming a chemically recyclable to monomers polymer as in any embodiment above, further comprising depolymerizing the formed chemically recyclable to monomers, polymer, wherein the resulting plurality of monomers comprises a plurality of cycloalkene-fused ring monomers in the lower energy state.

Another embodiment of the present invention provides a method of forming a chemically recyclable to monomers polymer as in any embodiment above, further comprising depolymerizing the formed recyclable block copolymer, wherein the resulting plurality of monomers comprises a plurality of cycloalkene-fused ring monomers in the lower energy state.

An embodiment of the present invention provides a method of synthesizing a monomer capable forming a polymer through ring-opening metathesis polymerization and capable of depolymerization thereafter through ring-closing metathesis, the method comprising providing a cyclic diene, and performing a photochemical 2+2 cycloaddition with an olefin to the cyclic diene to thereby form a cycloalkene-fused ring monomer comprising a cycloalkene having a fused ring attached thereto wherein the fused ring decreases the ring strain energy of the cycloalkene to a lower ring strain energy state of 5.3 kcal/mol or lower as compared to the same cycloalkene without the fused ring having a ring strain energy above 5.3 kcal/mol, wherein the fused ring is optionally functionalized, and wherein the cycloalkene of the cycloalkene-fused ring monomer is capable of isomerization into a higher ring strain energy state before polymerization.

Another embodiment of the present invention provides a method of synthesizing a monomer as in any embodiment above, further comprising the step of functionalizing the fused ring of the cycloalkene-fused ring monomer.

Another embodiment of the present invention provides a method of synthesizing a monomer as in any embodiment above, wherein functionalizing the fused ring of the cycloalkene-fused ring monomer includes providing fluorinated functional groups attached to the fused ring.

Another embodiment of the present invention provides a method of synthesizing a monomer as in any embodiment above, wherein functionalizing the fused ring of the cycloalkene-fused ring monomer includes esterification or forming an imide.

Another embodiment of the present invention provides a method of synthesizing a monomer as in any embodiment above, further comprising isomerizing the cycloalkene-fused ring monomer into the higher ring strain energy state before polymerization.

DETAILED DESCRIPTION OF ILLUSTRATIVE EMBODIMENTS

Figure 1:
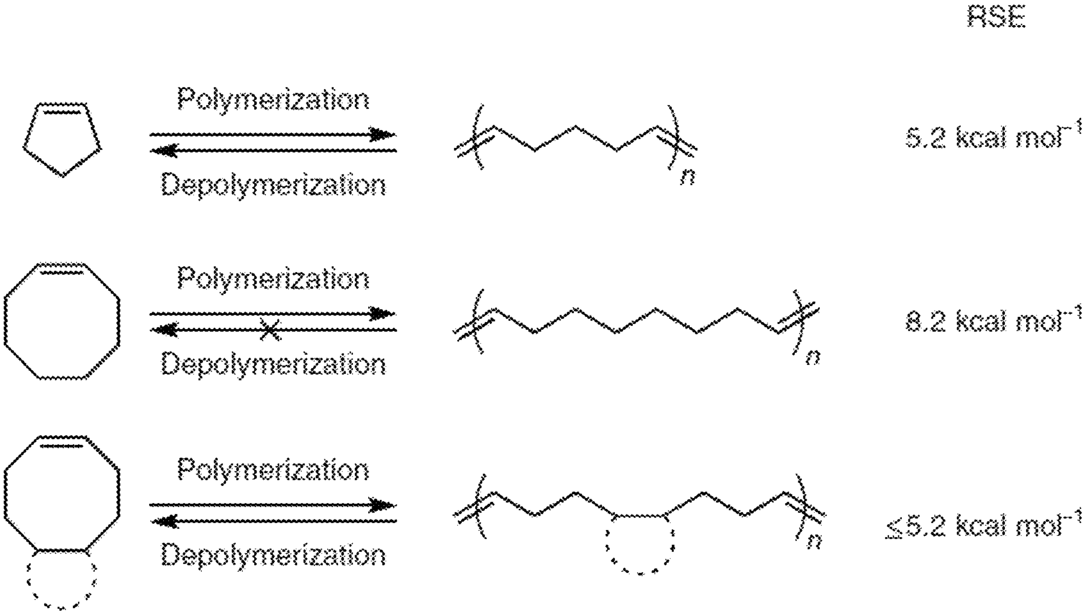
FIG. 1 provides a general schematic representation of the lowering of ring strain energy (RSE) of a cycloalkene to permit polymerization and depolymerization.

An objective of the present invention is to provide olefin metathesis-based chemically recyclable polymers enabled by fused-ring monomers. Ideally, cyclic monomers according to the present invention would have ring strain energies, RSEs, comparable to that of cyclopentene. The cyclic monomers according to the present invention may be polymerized through ring opening metathesis polymerization, and depolymerized through ring closing metathesis during recycling, which is readily favored when the RSE of the cyclic monomer is comparable to that of cyclopentene.

Chemically recyclable polymers of the present invention are formed through ring-opening metathesis of monomers wherein a fused ring is attached to a cycloalkene. The addition of the fused ring allows the polymer to be depolymerizable by reducing the RSE in the cycloalkene monomers from a value greater than 5.3 kcal $mol^{-1}$ (without fused ring) to a value equal to or lower than 5.3 kcal $mol^{-1}$ (with fused ring). In some embodiments involving cycloalkenes of 8 carbons or more, the cycloalkene is isomerized to convert the cycloalkene to a trans-configuration (also known as the corresponding E-cycloalkene). In some embodiments, the fused ring includes functionalization, and, in some particular embodiments, fluoride functionalization to yield chemically recyclable semi-fluorinated polymers that can be efficiently depolymerized under mild conditions. In some embodiments, the functionalization includes one or more terminal groups comprising fluorine.

In some embodiments, the cycloalkenes that are modified with the fused rings including from 7- to 12-membered rings. In some embodiments the cycloalkene is based on cycloheptene (7-membered ring). In some embodiments the cycloalkene is based on cyclooctene (8-membered ring). In some embodiments the cyclic olefin is based on cyclononene (9-membered ring). In some embodiments the cyclic olefin based on cylcodecene (10-membered ring). In some embodiments the cyclic olefin is based on cycloundecene (11-membered ring). In some embodiments the cyclic olefin is based on cycloduodecene (12-membered ring).

An 8-membered cyclic olefin is particularly attractive because functionalized cyclooctenes can typically be made from 1,5-cyclooctadiene, an inexpensive, commercially available starting material. As a result, polycyclooctene is one of the most extensively exploited polycycloalkenes.

In some embodiments the fused ring is a cycloalkane. Suitable fused rings for the present invention include 3-member to 6-membered fused rings. In some embodiments the fused ring is cyclopentane. In some embodiments the fused ring is cyclopentane. In some embodiments the fused ring is cyclopentane. In some embodiments the fused ring is cyclopentane. In some embodiments the fused ring is cyclohexane.

In some embodiments the fused ring is cis-fused or trans-fused. In some embodiments the fused ring is cis-fused. In some embodiments the fused ring is trans-fused.

In some embodiments, the fused ring is at least 2 carbon atoms removed from the double bond. In other embodiments, the fused ring is opposite the double bond or as closely opposite as possible for odd-membered rings. In some embodiments with a 7-membered cycloalkene, the fused ring is at the 3 and 4 position or the 4 and 5 position. In some embodiments with an 8-membered cycloalkene, the fused ring is at the 5 and 6 position. In some embodiments with a 9-membered cycloalkene, the fused ring is at the 5 and 6 position or the 6 and 7 position. In some embodiments with a 10-membered cycloalkene, the fused ring is at the 6 and 7 position. In some embodiments with an 11-membered cycloalkene, the fused ring is at the 6 and 7 position or the 7 and 8 position. In some embodiments with a 12-membered cycloalkene, the fused ring is at the 7 and 8 position.

Suitable cycloalkenes for the present invention can be identified by the generalized ring-closing metathesis reaction used to calculate the RSE of a cyclic olefin; the RSE for the cyclic olefin is essentially the enthalpy change for the ring-closing metathesis that affords the cyclic olefin, as shown in the exemplary scheme below.

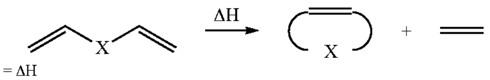

RSE = ΔH

In accordance with this invention, the addition of the fused ring serves to reduce the RSE in the cycloalkene monomers from a value greater than 5.3 kcal $mol^{-1}$, without the fused ring, to a value equal to or lower than 5.3 kcal $mol^{-1}$, with the fused ring. To identify a fused ring that can lower the ring strain of cyclooctene to the above-mentioned target, the RSEs of cyclooctenes with three-, four-, five- and six-membered rings fused at the 5 and 6 positions, including both cis and trans isomers, were calculated. The computation of RSE was conducted by calculating the enthalpy change of the RCM reaction using density functional theory at the B3LYP/6-31G(d,p) level, which provided reasonable predictions for the RSEs of cyclic olefins.

As shown in FIG. 1, polycyclopentene is depolymerizable, whereas polycyclooctene is not. The difference is caused by a higher RSE in cyclooctene. An appropriate ring (shown as a dashed line in FIG. 1) is provided in accordance with this invention to lower the RSE of cyclooctene to a level that is lower than or comparable to that of cyclopentene, enabling depolymerization of the polymer.

Figure 2:
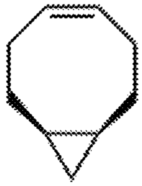
FIG. 2 provides a table showing structures and calculated RSEs for cyclooctene with 3-, 4-, 5- and 6-membered rings both cis- and trans-fused at the 5 and 6 positions.
Figure 2:
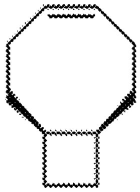
Figure 2:
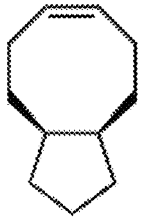
Figure 2:
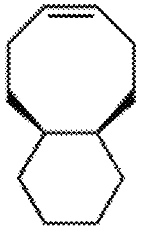
Figure 2:
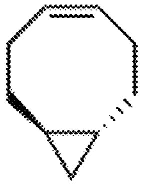
Figure 2:
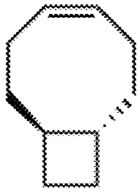
Figure 2:
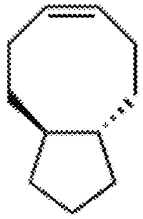
Figure 2:
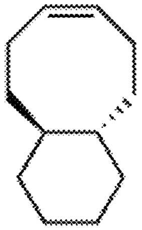
Figure 3:
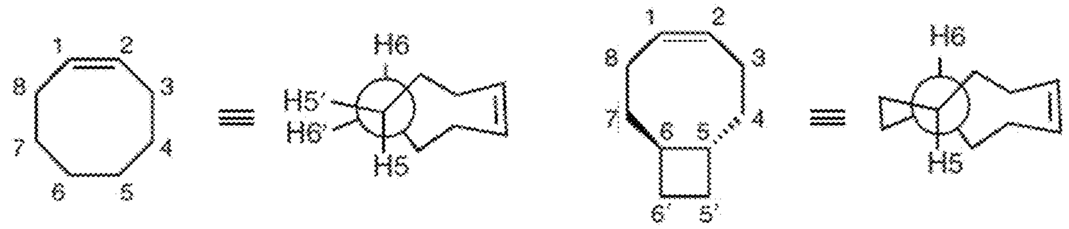
FIG. 3 provides the structures and corresponding Newman projections of cyclooctene and trans-cyclobutane-substituted cyclooctene showing the numbering scheme.
Figure 4:
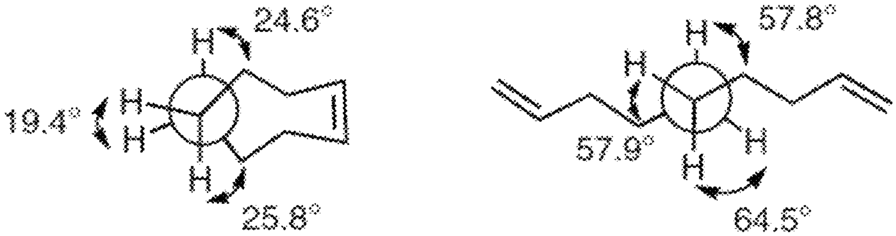
FIG. 4 provides the projections for non-substituted, trans-cyclobutane (trans-CB)-substituted and cis-cyclobutane H5-C5-C6-C7 and H6-C6-C5-C4, as well as H5'-C5-C6-C6' (for the case with no substitution) and C5'-C5-C6-C6' (for the cases involving CB substitution), are shown along with the projections.
Figure 4:
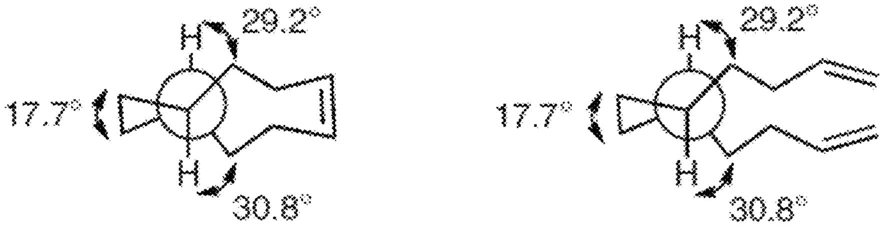
Figure 4:
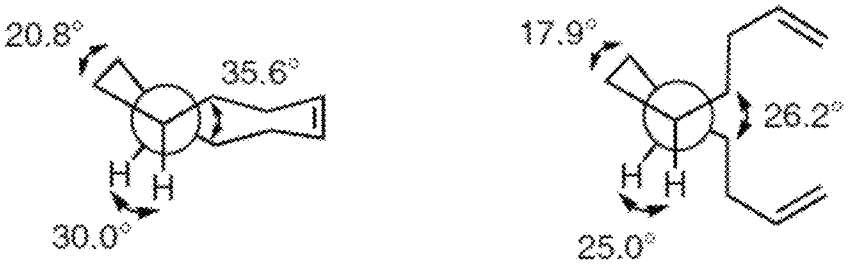
Figure 5:
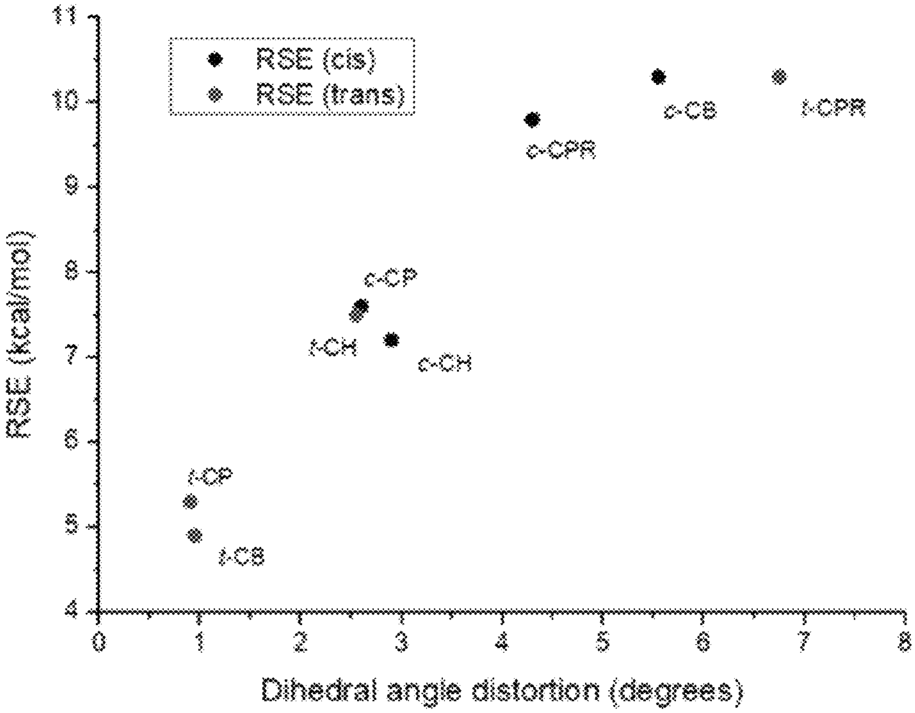
FIG. 5 provides a chart showing the correlation between the ring strain energy and the distorted dihedral angles C4-C5-C5'-C6 and C7-C6-C6'-C5 from the acyclic diene to the cycloalkane-fused cyclooctene, where the ring strain energy is plotted against the distorted dihedral angles for each cycloalkane-fused cyclooctene.

By way of example, the calculated RSEs for cyclooctene with 3-, 4-, 5- and 6-membered rings both cis- and trans-fused at the 5 and 6 positions are shown in FIG. 2.

In some embodiments, the fused rings are functionalized. Functionality may be selected to alter thermomechanical properties of the resulting polymer. Examples of such thermomechanical properties include $T_d$ and $T_g$ which may be increased or decreased according to the functionality included on the fused ring. Generally, cyclic functional groups exhibit higher $T_g$ than acyclic function groups. Additionally, longer alkyl chains provide polymers with a lower $T_g$ than shorter alkyl chains.

An objective of the present invention is to provide olefin metathesis-based chemically recyclable semi-fluorinated polymers enabled by fused-ring monomers. These polymers exhibit high thermal stability, hydrophobicity, and tunable thermomechanical properties. In addition, the present invention provides for block copolymers that comprise a semi-fluorinated block and a block containing poly(ethylene glycol) (PEG) side chains. Further, the present invention provides for post-functionalization of a pentafluorophenyl imide functionalized polymer demonstrating the ability to further modify the system.

Chemically recyclable monomers according to the present invention may be synthesized according to the description above regarding [2+2] photocycloaddition and further including esterification or reaction with pentafluoroaniline to generate an imide. Further, the [2+2] photocycloaddition may be carried out using alternative reactants to produce functionalized fused rings trans-fused to a cycloalkene.

In some embodiments of the present invention, functionalization of the fused ring of monomers according to the present invention provides for semi-fluorinated polymers after performing living ROMP. Advantageously, semi-fluorinated polymers according to the present invention are chemically recyclable to monomers in the presence of a catalyst under ambient conditions.

In some embodiments, polymers formed from living ROMP of monomers according to the present invention may be functionalized post-polymerization. In some embodiments, post-polymerization functionalization is achieved through a nucleophilic aromatic substitution. In some embodiments nucleophilic aromatic substitution includes ($S_NAr$) of the para-fluoro atom in the pentafluorophenyl unit with an aromatic thiol. The mild conditions, quantitative conversion, and regiospecific substitution at the para-fluoro position together make this reaction particularly useful for post-polymerization functionalization.

Figure 6:
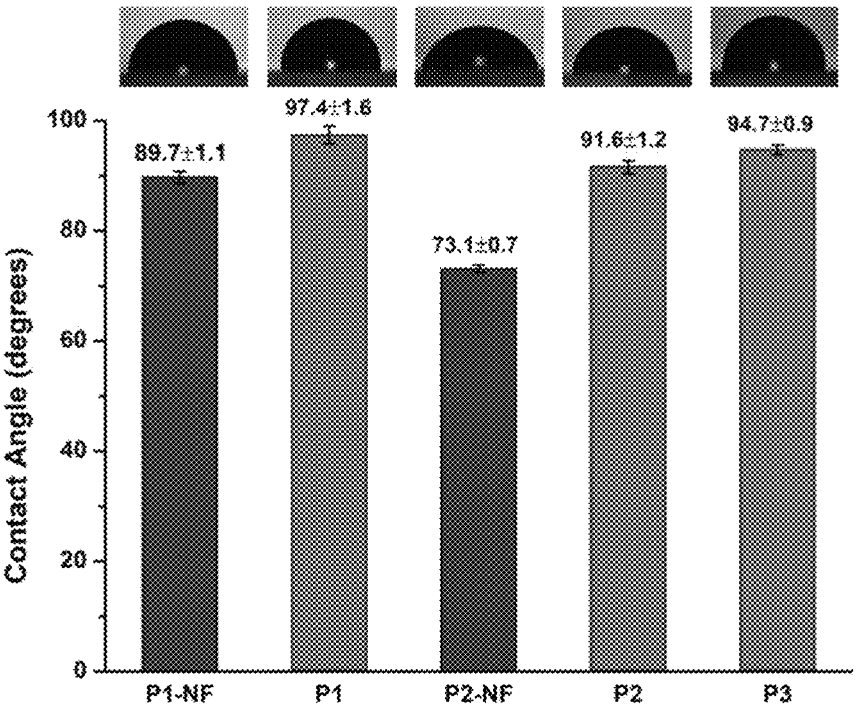
FIG. 6 provides a chart and images showing the water contact angles for various polymers.

As shown in FIG. 6, semi-fluorinated polymers formed from monomers of according to the present invention exhibit increased water contact angles over their corresponding non-semi-fluorinated polymer.

Based on the difference in RSE between the fused rings and the unsubstituted cyclooctene (RSE=8.2 kcal $mol^{-1}$), the calculated results can be sorted into three groups:

1. RSEs that are higher than that of the virgin cyclooctene, including cis-cyclopropane-, trans-cyclopropane- and cis-cyclobutane-fused cyclooctenes
2. Fused rings with slightly decreased ring strain, including cis-cyclopentane-, cis-cyclohexane- and trans-cyclohexanefused cyclooctenes
3. Cycloalkane-fused cyclooctenes having the lowest RSEs and having RSEs that are lower than or comparable to that of cyclopentene (RSE=5.2 kcal $mol^{-1}$), including trans-cyclobutane and trans-cyclopentane-fused cyclooctenes The calculated RSEs of the ROMP polymers of the trans-cyclobutane-fused cyclooctenes and trans-cyclopentane-fused cyclooctenes indicate that the obtained polymers from these monomers are suitable for catalytic depolymerization in a way similar to polypentenamers.

A further objective of the present invention is to provide olefin metathesis-based chemically recyclable polymers enabled by fused-ring monomers and cis-to-trans alkene isomerization. Ideally, cyclic monomers according to the present invention would have ring strain energies, RSEs, comparable to that of cyclopentene. The cyclic monomers according to the present invention may be polymerized through ring opening metathesis polymerization, and depolymerized through ring closing metathesis during recycling, which is readily favored when the RSE of the cyclic monomer is comparable to that of cyclopentene. Ring opening metathesis polymerization is readily favored after cis-to-trans alkene isomerization of the cyclic monomer.

Polymerization is limited at near-equilibrium (monomer/polymer concentration) conditions in low ring strain cycloalkene systems. This limits full conversion polymerization. Further, the reduced driving force during polymerization inhibits synthesizing block copolymers as including a second monomer dilutes the first monomer, causing depolymerization of the first block.

A polymerization system based on near-equilibrium polymerization and/or depolymerization is characterized by low driving force in polymerization. Isomerizing the monomer into a high-energy state, i.e. increasing the ring strain energy of the cycloalkene fused ring system, enables high driving force during polymerization, and the resulting polymer can advantageously depolymerize back into the low-energy state monomer, i.e. low ring strain energy configuration.

In some embodiments, focusing particularly on those monomers in accordance with this invention having an 8-membered or higher cycloalkene, the ring strain of the monomer is increased by isomerization of the cycloalkene from a cis-alkene to a trans-alkene, which would also be appreciated at least in some embodiments as isomerization from a Z-alkene to an E-alkene at the cycloalkene. This is generally shown in FIG. 7 employing cyclooctene by way of example.

Figure 7:
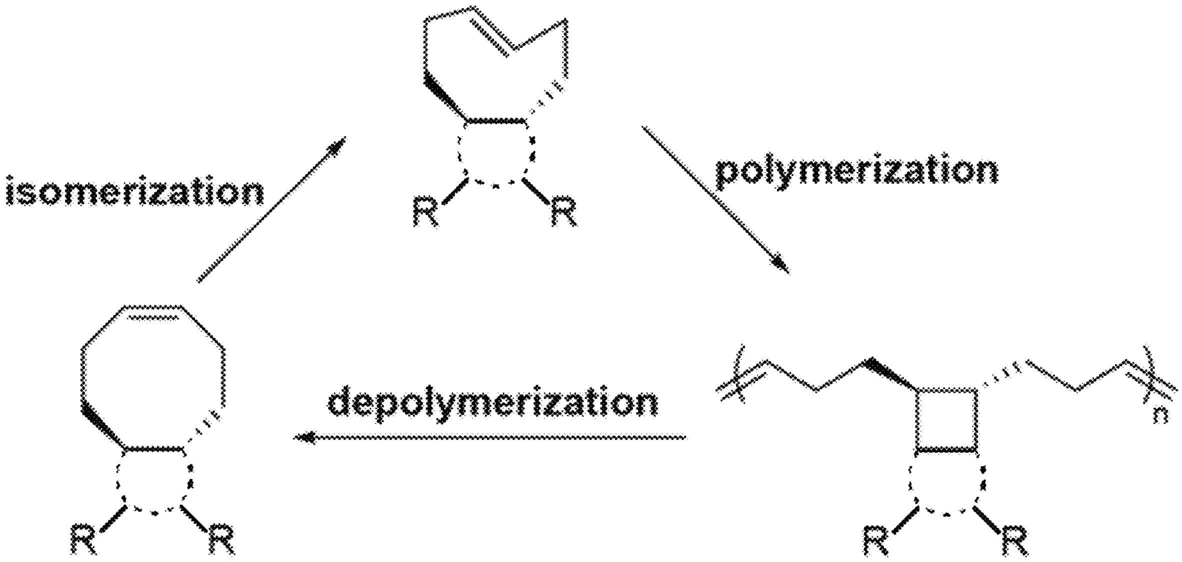
FIG. 7 provides a general schematic representation of the entire life cycle of monomers, including isomerization, polymerization, and depolymerization.

As seen in FIG. 7, cyclooctene, also called Z-cyclooctene (cis-cyclooctene), is converted to an E-cyclooctene (trans-cyclooctene). This increases ring strain energy and promotes kinetic-driven ROMP in the presence of a ruthenium catalyst. As a result of this increased driving force during polymerization full polymerization conversation at lower initial monomer concentrations is possible. Further, the resulting corresponding polymer maintains chemical recyclability to monomers during mild depolymerization to advantageously form the low ring strain energy state monomer.

In one or more embodiments, isomerizing the monomers according to the present invention may be performed according to conventional and known methods in the art. Suitable methods isomerization techniques preserve the functionality that may be present on the fused ring included in monomers according to the present invention.

Isomerization techniques relating to olefin inversion include direct isomerization, including thermal-chemical isomerization and photoisomerization, oxidative additions to alkenes followed by reductive elimination, cleavage of epoxides followed by anti or syn elimination, fragmentation of thiiranes and related heterocycles, fragmentation of aziridines and related heterocycles, fragmentations of heterocycles based on vic-diols, dithiols, and interconversion of other alkene geometrical isomers.

In some embodiments, isomerization of the cycloalkene-fused ring monomer is performed using a three-step sequence involving epoxidation, formation of β-hydroxy diphenylphosphine oxide, and elimination. This isomerization method is not compatible with ester and imide functional groups.

In some embodiments, isomerization of the cycloalkene-fused ring monomer is performed using photochemical isomerization in the presence of silver nitrate, which selectively binds to the trans-cycloalkene to form a water-soluble metal complex. Subsequent demetallation via washing with ammonium hydroxide provides the trans-cycloalkene-fused ring monomer. This method of isomerization is compatible with many functional groups that may be present on the fused ring including hydroxyl, esters, and imides. Further, the method involves a single-step reaction. Batch processing according to this method has low yields (less than 10%) due to photodegradation of the trans-cycloalkene-fused ring monomer. Performing this method using a continuous flow column improves yields due to reduced photodegradation (exposure to UV light) effects. Thus, it is advantageous to use continuous processing to avoid photodegradation of the trans-cycloalkene-fused ring monomer.

In some embodiments, the cycloalkene-fused ring monomer is polymerized using living ROMP including using a catalyst as an initiator, a weakly coordinating ligand, a coordinating solvent.

In some embodiments, suitable catalysts for living ROMP include ruthenium catalysts. In these and other embodiments ruthenium catalysts include first-generation, second-generation, third-generation Grubbs catalysts, as well as first-generation and second-generation Hoveyda-Grubbs catalysts. Polymers formed from the cycloalkene-fused ring monomer are capable of undergoing depolymerization in the presence of a ruthenium catalyst. Living ROMP will proceed without depolymerization when certain conditions are met using a ruthenium catalyst.

In embodiments of the present invention using ruthenium catalysts for living ROMP of the isomerized cycloalkene-fused ring monomer, living ROMP is considered to proceed without depolymerization when the polymerization percentage is 90% or greater. In other embodiments, when the polymerization is 91% or greater. In other embodiments, when the polymerization is 92% or greater. In other embodiments, when the polymerization is 93% or greater. In other embodiments, when the polymerization is 94% or greater. In other embodiments, when the polymerization is 95% or greater. In other embodiments, when the polymerization is 96% or greater. In other embodiments, when the polymerization is 97% or greater. In other embodiments, when the polymerization is 98% or greater. In other embodiments, when the polymerization is 99% or greater.

In embodiments of the present invention using ruthenium catalysts for living ROMP of the isomerized cycloalkene-fused ring monomer, living ROMP is considered to proceed without depolymerization when the depolymerization percentage is 5% or lower. In other embodiments, when the depolymerization percentage is 4% or lower. In other embodiments, when the depolymerization percentage is 3% or lower. In other embodiments, when the depolymerization percentage is 2% or lower. In other embodiments, when the depolymerization percentage is 1% or lower.

The initial concentration of monomer directly relates to the overall conversion to polymer during living ROMP. The present invention advantageously allows for reduced initial higher RSE monomer concentrations that allow for living ROMP to proceed without depolymerization relative to the lower RSE monomer. Polymerization of the non-isomerized monomers according to the present invention required concentrations of 2.0M or greater.

In embodiments of the present invention employing isomerized monomer, the initial monomer concentration is at least 0.010M. In other embodiments, the initial monomer concentration is at least 0.015M. In other embodiments, the initial monomer concentration is at least 0.020M. In other embodiments, the initial monomer concentration is at least 0.025M. In other embodiments, the initial monomer concentration is at least 0.030M.

In embodiments of the present invention using ruthenium catalysts for living ROMP of the isomerized cycloalkene-fused ring monomer, the monomer/initiator ratio is at least 400/1. In other embodiments, the monomer/initiator ratio is at least 350/1. the monomer/initiator ratio is at least 300/1. the monomer/initiator ratio is at least 250/1.

Polymers formed from monomers according to the present invention exhibit low polydispersity. Low polydispersity is characterized by a dispersity, D, of less than 1.3. Low dispersity indicates control over the molecular weight of the polymer. The dispersity of the polymer is affected by the catalyst to weakly coordinating ligand ratio.

In some embodiments, a weakly coordinating ligand is used during living ROMP to provide control over the molecular weight distributions of the formed polymer. In embodiments of the present invention using a weakly coordinating ligand during living ROMP, the amount of weakly coordinating ligand is at least 10 equivalents or greater than the amount of catalyst. In other embodiments, the amount of weakly coordinating ligand is at least 15 equivalents or greater than the amount of catalyst. In other embodiments, the amount of weakly coordinating ligand is at least 20 equivalents or greater than the amount of catalyst. In other embodiments the amount of weakly coordinating ligand is at least 25 equivalents or greater than the amount of catalyst.

Weakly coordinating ligands (also known as weak field ligands) present during living ROMP suppress secondary metathesis. Weakly coordinating ligands from complexes with the catalyst. A suitable weakly coordinating ligand suitable for use with monomers according to the present invention is triphenylphosphine ($PPh_3$). Other weakly coordinating ligands known in the art are acceptable to suppress secondary metathesis.

Coordinating solvents used during living ROMP were observed to control polymerization of the monomers according to the present invention. Further, mixed solvents are acceptable allowing for dissolving of certain monomers or polymers that may not dissolve in one type of coordinating solvent, thereby improving polymerization. Two suitable coordinating solvents include at least tetrahydroguran (THF), dichloromethane (DCM). Other suitable coordinating solvents known in the art are acceptable to control polymerization of monomers according to the present invention.

Isomerized, high RSE state monomers according to the present invention have improved driving force during living ROMP that formation of block copolymers is enabled. Block copolymer synthesis includes formation of a first block polymer under the conditions for living ROMP described above, followed by synthesis of a second block polymer covalently bonded to the first block polymer. Isomerization of the monomers according to the present invention is required for block copolymer synthesis using monomers according to the present invention. An exemplary block copolymer synthetic scheme is depicted below.

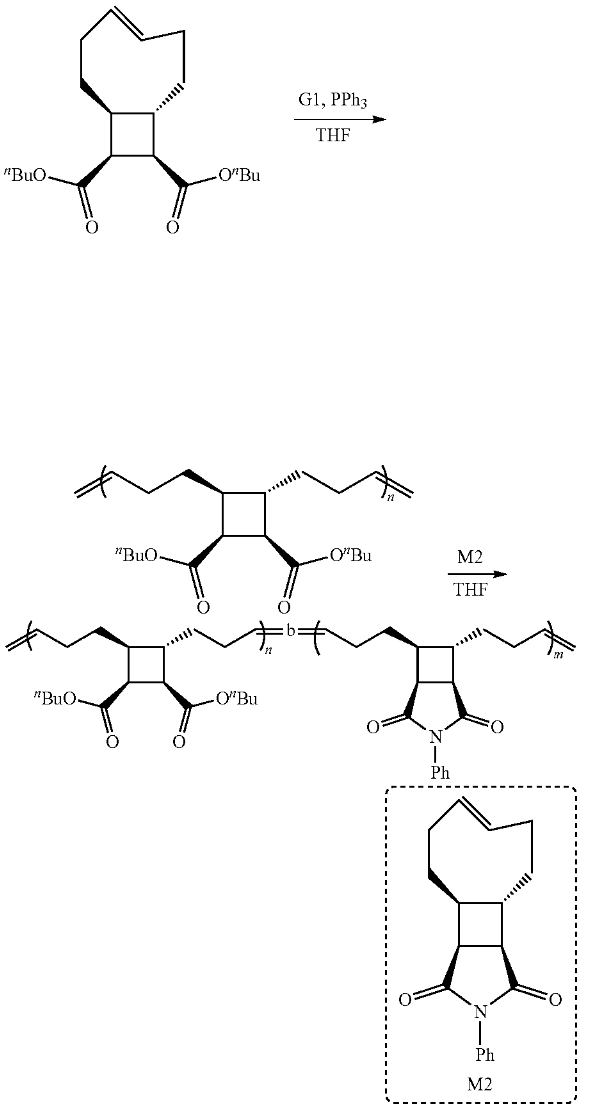

In some embodiments, amphiphilic block copolymer synthesis provides for living ROMP of monomers according to the present invention and an incompatible block polymer to enable self-assembly of the block copolymer into micellar structures in solvents. An exemplary block copolymer is depicted below wherein a hydrophobic block formed from semi-fluorinated monomers according to the present invention forms a block copolymer with a hydrophilic PEG block.

P1-b-P4

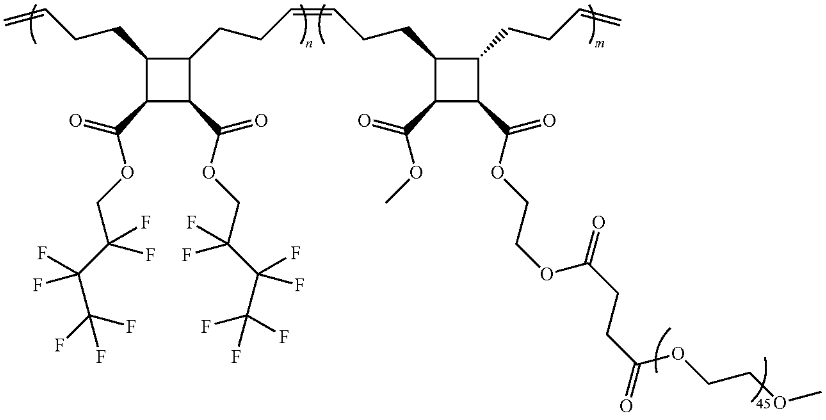

Advantageously, block copolymers synthesized from monomers according to the present invention are chemically recyclable to monomers. During depolymerization, the resulting monomers are in the low RSE state, which may then be isomerized for future use in polymers. Further, when the fused ring of monomers according to the present invention are fluorinated or semi-fluorinated, amphiphilic block copolymer synthesis is possible.

EXAMPLES

Example I

IA. Cis-Alkene Monomer Synthesis

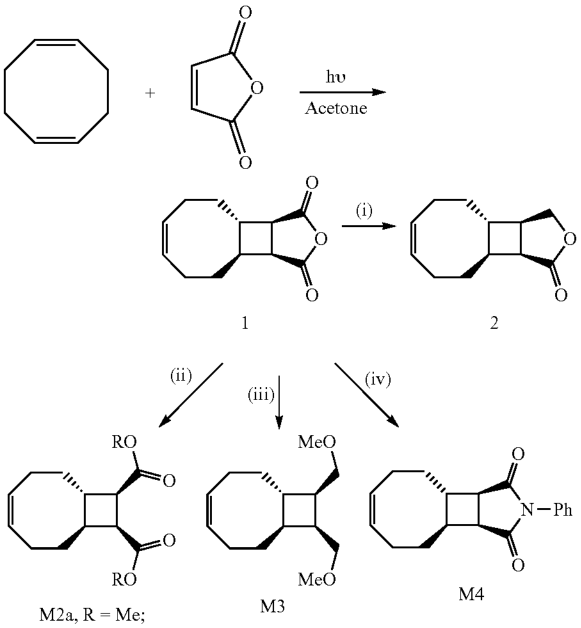

1 2

M2a, R = Me; M2b, R = $^{n}$Bu M3 M4

M1 was synthesized through a photochemical [2+2] cycloaddition of 1,5-cyclooctadiene and maleic anhydride followed by $LiAlH_4$ reduction. Note that the cyclobutane in M1 is trans-fused to the cyclooctene, indicating a cis-to-trans isomerization of the alkene prior to cycloaddition. Similar inversion of stereochemistry has been observed in other systems. Importantly, the moiety of trans-cyclobutane-fused cyclooctene (tCBCO) is exactly the target moiety. Aside from lactone, tCBCOs with other functional groups—including the diesters M2a and M2b, the diether M3 and the imide M4—were conveniently derived from the intermediate anhydride 1.

According to the scheme above, the intermediate anhydride 1 can be readily converted to M1, M2, M3 and M4 through conditions (i), (ii), (iii) and (iv), respectively. (i) 0.5 equiv. $LiAlH_4$, THF. (ii) M2a: MeOH, reflux; MeOH, EDC, DMAP, DCM. M2b: NaOH, $H_2O$, 60° C.; 1-butanol, EDC, DMAP, DCM. (iii) 1.0 equiv. $LiAlH_4$, THF; NaH, MeI, THF. (iv) Aniline, acetone; sodium acetate, acetic anhydride, 100° C.

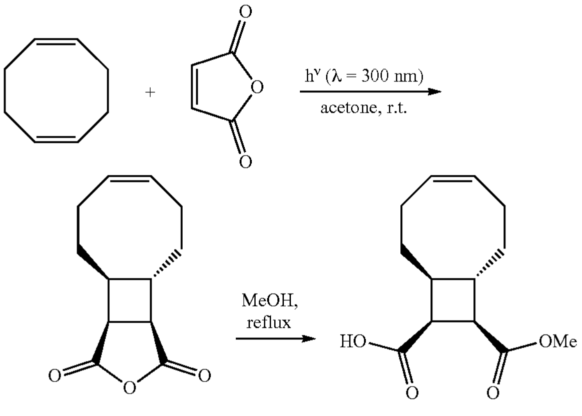

1 2

Synthesis of Ester-Acid 2 was performed according to the following procedure: To a quartz flask equipped with a stir bar, a solution of maleic anhydride (5.4 g, 55.1 mmol, 1 eq.) and cyclooctadiene (6.55 g, 61 mmol, 1.1 eq.) in acetone (150 mL) was added. The solution was sparged with nitrogen for ~30 min. followed by irradiation with 300 nm UV light in a Rayonet photoreaction chamber for 14 h. The mixture was then concentrated on a rotavap and the intermediate 1 was used without purification for the next step. The mixture that contains 1 was suspended in methanol (150 mL), and the mixture was refluxed for 3.5 h. The mixture was filtered, and the filtrate was concentrated by solvent evaporation using a rotavap and purified by column chromatography (3:7 ethyl acetate (EA)/hexane as eluent), followed by recrystallisation from an EA-hexane solution to yield methyl ester 2 as a white crystalline powder.

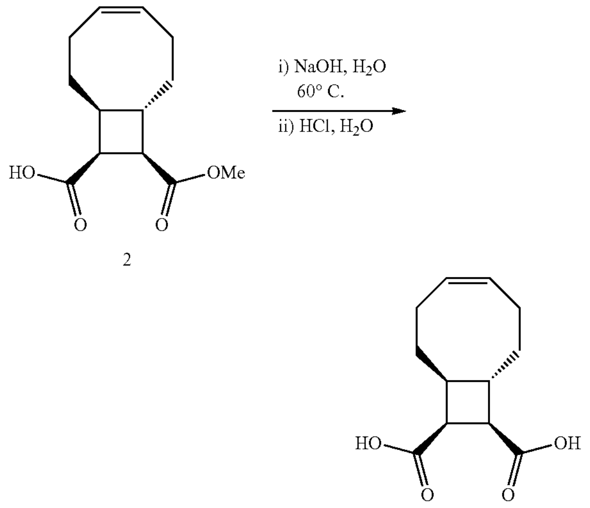

2

3

Synthesis of Diacid 3 was performed according to the following procedure: To a 50 mL round-bottom flask equipped with a stir bar, a solution of NaOH (1.68 g, 42 mmol, 16.7 eq.) in D.I. water (20 mL) was added. To the NaOH solution was added 600 mg of methyl ester-acid 2 (600 mg, 2.52 mmol, 1 eq.). The reaction was placed in an oil bath at 60° C. overnight (~14 h). The reaction mixture was then placed in an ice bath and neutralized with 3 N HCl. The aqueous phase was extracted with EA and the extraction was dried over Na2SO4, and filtered, followed by removal of solvent on a rotavap. The diacid 3 was obtained as a white powder.

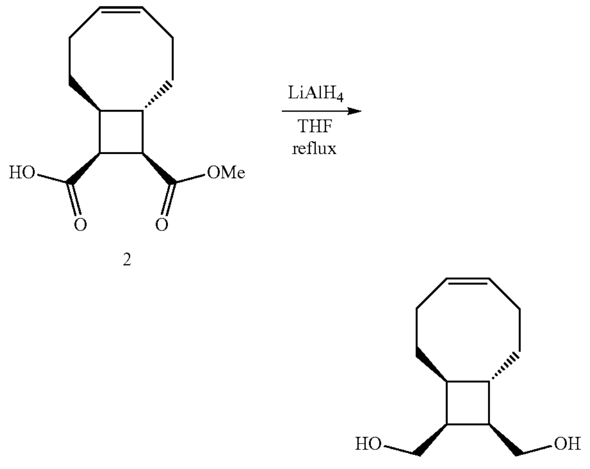

2

4

Synthesis of tCBCO diol 4 was performed according to the following procedure: A suspension of LiAlH4 (2.17 g, 57.07 mmol, 6.8 equ.) in dry THF (20 mL) was cooled in an ice bath. To the solution was added a solution of acid-ester 2 (2.00 g, 8.39 mmol, 1 equ) in dry THF (80 mL) dropwise. After stirring at 0° C. for 30 min, the reaction mixture was heated to reflux and left reflux overnight. The reaction mixture was cooled to 0° C., and quenched by adding 2.2 mL H2O, followed by addition of 2.2 mL 15% aqueous NaOH and 2.2 mL H2O. The suspension was filtered through Celite, and the filtrate was concentrated at reduced pressure. The resulting crude product was purified via column chromatography to afford diol 4 as a white solid (yield: 97.5%).

Synthesis of M2a was performed according to the following procedure: To a round-bottom flask equipped with a stir bar, methyl ester-acid 2 (600 mg, 2.52 mmol, 1 eq.), DMAP (61 mg, 0.5 mmol, 0.2 eq.), methanol (0.161 mg, 5.04 mmol, 2 eq.) and dry DCM (25 mL) were added. The solution was cooled over an ice bath and EDC (966 mg, 5.04 mmol, 2 eq.) was added. The mixture was allowed to warm to room temperature and stir overnight. The reaction mixture was then diluted with more DCM and washed with brine, dried over Na2SO4, filtered, and concentrated by solvent evaporation on a rotavap. The crude product mixture was purified via column chromatography, using a 1:4 EA/hexane mixture as eluent. After solvent removal, the product M2a was obtained as a white solid (509 mg, yield: 80%).

Synthesis of M2b was performed according to the following procedure: To a round-bottom flask equipped with a stir bar, diacid 3 (941 mg, 4.20 mmol, 1 eq.), DMAP (205.5 mg, 1.68 mmol, 0.4 eq.), butanol (684.9 mg, 9.24 mmol, 2.2 eq.) and dry DCM (60 mL) were added. The solution was cooled over an ice bath and EDC (3220.6 mg, 16.8 mmol, 4 eq.) was added. The mixture was allowed to warm to room temperature and stir overnight. The reaction mixture was then diluted with more DCM and washed with brine, dried over Na2SO4, filtered, and concentrated by solvent evaporation on a rotavap. The crude product mixture was purified via column chromatography, using a 1:9 EA/hexane mixture as eluent. After solvent removal, the product M2b was obtained as a clear, colorless oil. Yield: 540 mg (~38.3%).

Synthesis of M3 was performed according to the following procedure: To a solution of diol 4 (100.0 mg, 0.51 mmol, 1 eq.) in 5 mL THF was added sodium hydride (37.0 mg, 1.53 mmol, 3 eq.) at 0° C. After stirring for 3 h, iodomethane (95 μL, 1.53 mmol, 3 eq.) was added and the reaction was stirred at room temperature for 1 h. 20/80 MeOH/H2O was then added to quench the reaction and the mixture was extracted with DCM. The organic phase was washed with brine and dried over sodium sulfate. The crude product was purified via column chromatography (15% EA/hexane) to afford 96 mg M3 as a clear, colorless liquid (yield: 84%).

Synthesis of M1 was performed according to the following procedure: Since 1 obtained directly from photochemical [2+2] cycloaddition is difficult to purify, a purer 1 was obtained from the diacid 3. This practice was found to ease the purification for the synthesis of M4. In a flask charged with diacid 3 (2.00 g, 8.92 mmol) was added acetic anhydride (20 mL) and refluxed overnight. Acetic anhydride was removed via vacuum distillation to afford the white solid anhydride 1. The anhydride was used without further purification. Anhydride 1 was dissolved in acetone (8 mL), and aniline (1.63 mL, 17.84 mmol, 2.0 eq.) was added dropwise to the solution. White precipitate formed gradually, and the mixture became mud-like after 1 h. The reaction was allowed to proceed for another 2 h before suction filtration. The solid was washed with acetone and dried under vacuum, affording the amic acid as a white solid (2.50 g). The amic acid was added to a mixture of sodium acetate (1.10 g, 13.38 mmol, 1.5 eq.) and acetic anhydride (15 mL). The suspension was heated overnight at 100° C. and became clear gradually. The mixture was poured into ice water, and the resulting precipitate was collected through suction filtration. The solid was further washed with water, dissolved in DCM, and dried over sodium sulfate. The crude product was purified via column chromatography using DCM. The product was further purified through recrystallisation in toluene, affording the imide monomer M4 as white crystals (1.2 g, overall yield: 47.6%).

Example II

IIA. Trans-Alkene Monomer Synthesis

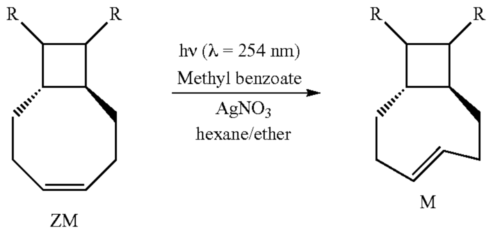

ZM

M

ZM1, ZM2 and ZM3 were synthesized according to methods provided above (In Example I) for related previously reported procedures for M2b, M4, and M2a, respectively. The isomerization from ZM to M were performed following similar procedures, with an example using ZM1 shown below:

ZM1 (2.81 g, 8.36 mmol, 1 equiv) and methyl benzoate (2.27 g, 16.72 mmol, 2 equiv) were dissolved in a 2:3 v/v $Et_2O$/hexane solvent mixture (pure $Et_2O$ used for M2 and 1:1 v/v $Et_2O$/hexane for M3) in a quartz tube. A column was first filled with a small amount of normal silica gel at the bottom to prevent silver leaking and then filled with 10 wt % $AgNO_3$-impregnated silica gel (2.84 g $AgNO_3$, 16.72 mmol, 2 equiv). The reaction mixture was irradiated overnight with 254 nm UV light in a Rayonet photoreaction chamber with 16 RPR-2537A lamps, and meanwhile, it was circulated through the above-mentioned column using a metering pump.

To deactivate the $AgNO_3$ impregnated silica gel and separate out the crude product, the silica gel in the column was pushed out into a flask, which was filled with 300 mL aqueous ammonia solution and 300 mL dichloromethane (DCM). The mixture was stirred for 15 min and diluted with 200 mL water. The organic phase was collected, and the aqueous phase was further extracted with dichloromethane for 3 times. The combined organic phase was washed with water and brine and dried over sodium sulfate. After filtration and removal of solvent, the resulting yellow oil was then run through a short column with $AgNO_3$ impregnated silica gel and $AgNO_3$ impregnated TLC was performed to ensure the removal of ZM1. The $AgNO_3$ impregnated silica gel in the short column was then deactivated by repeating the procedures described above. The resulting mixture was then run through a short plug of silica gel. The solvent was removed on a rotovap, and the sample was further dried on a vacuum line while being cooled in a liquid nitrogen bath, affording pure M1 (0.93 g, yield: 33%) as white solid.

The yields for M2 and M3 were 30% and 81%, respectively.

M1, M2 and M3 obtained were all mixtures of two diastereomers, and the mixtures of diastereomers were used directly for polymerization studies.

M1

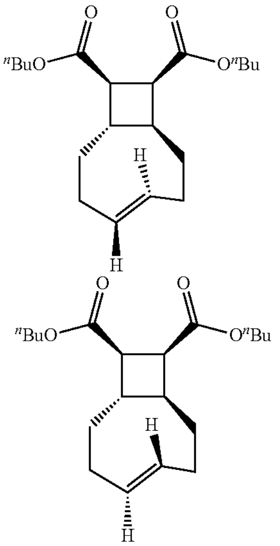

M1

$^1$H NMR (500 MHz, $CDCl_3$, ppm): δ 5.94-5.67 (m, 0.4H), 5.60-5.39 (m, 1.6H), 4.04 (m, 4H), 3.34 (t, J=9.0 Hz, 0.8H), 3.32-3.26 (t, J=8.6, 0.2H), 2.72 (m, 0.2H), 2.64-2.47 (m, 1.8H), 2.43-1.88 (m, 4H), 1.84-1.72 (m, 1H), 1.69-1.45 (m, 8H), 1.44-1.18 (m, 4H), 0.93 (dt, J=9.0, 7.4 Hz, 6H). $^{13}$C NMR (125 MHz, $CDCl_3$, ppm): δ 172.9, 172.8, 172.7, 172.6, 136.8, 135.1, 134.6, 134.5, 64.3, 64.3, 64.2, 64.1, 46.4, 45.5, 45.3, 43.9, 43.8, 43.2, 42.9, 42.2, 41.3, 40.7, 36.1, 35.8, 33.3, 33.1, 30.8, 30.8, 30.7, 30.7, 26.1, 25.8, 19.3, 19.3, 19.2, 19.2, 13.8, 13.8, 13.8, 13.8. HRMS-ESI (m/z): calcd for $C_{20}H_{32}NaO_4^+$ [M+Na]$^+$, 359.2193; found, 359.2159.

M2

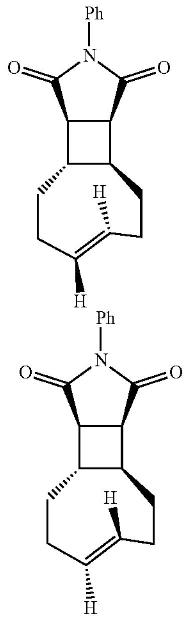

M2

$^1$H NMR (500 MHz, $CDCl_3$, ppm): δ 7.52-7.45 (m, 2H), 7.43-7.36 (m, 1H), 7.33-7.28 (m, 2H), 5.89-5.64 (m, 0.3H), 5.61-5.40 (m, 1.7H), 3.33 (dd, J=10.6, 6.9 Hz, 0.8H), 3.28 (dd, J=10.2, 6.5 Hz, 0.2H), 2.97-2.87 (m, 1H), 2.64-2.29 (m, 3H), 2.30-2.19 (m, 2H), 2.19-2.00 (m, 3H), 1.97-1.72 (m, 1H), 1.61-1.49 (m, 1H). $^{13}C$ NMR (125 MHz, $CDCl_3$, ppm): δ 178.6, 178.3, 177.2, 176.7, 134.1, 134.1, 133.8, 133.8, 132.3, 132.3, 129.2, 129.2, 129.2, 129.2, 128.6, 128.6, 128.6, 128.6, 128.6, 128.6, 50.3, 48.7, 44.3, 44.3, 43.0, 41.5, 40.9, 40.0, 39.7, 39.2, 36.3, 36.1, 35.7, 33.6, 33.4, 33.4. HRMS-ESI (m/z): calcd for $C_{18}H_{19}NaNO_2^+$ [M+Na]$^+$, 304.1308; found, 304.1283.

M3

M3

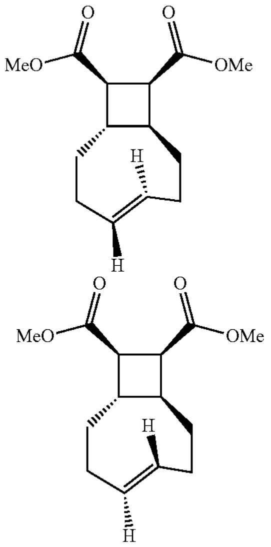

$^1H$ NMR (500 MHz, $CDCl_3$, ppm): δ 5.91-5.69 (m, 0.5H), 5.57-5.43 (m, 1.5H), 3.70-3.60 (m, 6H), 3.37 (t, J=9.1 Hz, 0.75H), 3.32 (t, J=8.6 Hz, 0.25H), 2.76-2.48 (m, 2H), 2.42-1.89 (m, 6H), 1.83-1.45 (m, 3H). $^{13}C$ NMR (125 MHz, $CDCl_3$, ppm): δ 173.3, 173.2, 134.6, 134.5, 51.5, 51.4, 45.5, 43.8, 42.8, 42.0, 41.2, 35.8, 33.3, 33.1. HRMS-ESI (m/z): calcd for $C_{14}H_{20}NaO_4^+$ [M+Na]$^+$, 275.1254; found, 275.1266.

IIB. Synthesis of Polymers from Trans-Alkene Monomers

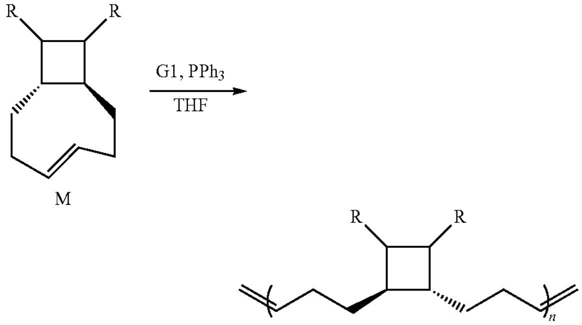

All polymerization studies were conducted in a $N_2$-filled glovebox. Stock solutions of M1, $PPh_3$ and G1 in THF were prepared in the glovebox. All vials and stir bars were dried in an oven overnight before polymerization.

(1) Homopolymers P1-P3

An example of polymerization using M1 is shown below. The procedure for polymerizing M1 was as follows: To a vial charged with a stir bar was added M1 (517 mg, 1.19 mmol, 1.0 equiv) and $PPh_3$ (60.5 mg, 0.18 mmol, 0.15 equiv) from their stock solutions. Additional THF was added to reach a monomer concentration of 0.25 M. G1 (3.16 mg, 2.97 μmol, 0.0025 equiv) was added, and the mixture was stirred for 10 min before ethyl vinyl ether (1 mL) was added. The mixture was stirred for additional 30 min. The polymer was precipitated in methanol for three times and dried on a vacuum line overnight before $^1H$ NMR and GPC characterization.

P1

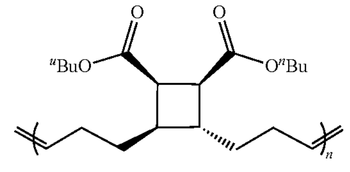

$^1H$ NMR (500 MHz, $CDCl_3$, ppm) δ 5.47-5.18 (m, 2H), 4.14-3.97 (m, 4H), 3.46-3.36 (m, 1H), 2.78-2.58 (m, 2H), 2.16-1.83 (m, 5H), 1.67-1.28 (m, 12H), 1.01-0.88 (m, 6H).

P2

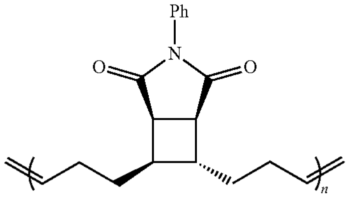

$^1H$ NMR (500 MHz, $CDCl_3$, ppm) δ 7.49-7.41 (m, 2H), 7.41-7.32 (m, 1H), 7.32-7.26 (m, 2H), 5.51-5.26 (m, 2H), 3.50-3.24 (m, 1H), 3.09-2.80 (m, 1H), 2.70-2.34 (m, 1H), 2.32-1.89 (m, 4H), 1.81-1.50 (m, 4H), 1.48-1.34 (m, 1H).

P3

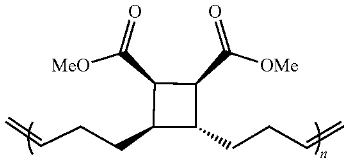

$^1H$ NMR (500 MHz, $CDCl_3$, ppm) δ 5.45-5.20 (m, 2H), 3.67 (s, 3H), 3.65 (s, 3H), 3.48-3.39 (m, 1H), 2.80-2.70 (m, 1H), 2.70-2.58 (m, 1H), 2.17-1.82 (m, 5H), 1.59-1.34 (m, 4H).

(2) Block Copolymer P1-b-P2

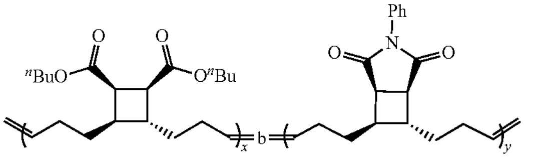

M1 (9.57 mg, 28.5 μmol, 1.0 equiv) and $PPh_3$ (2.24 mg, 8.5 μmol, 0.3 equiv) were added to two vials (vial A, B). THF was added to each vial to reach a monomer concentration of 0.25 M. G1 (0.1171 mg, 0.14 μmol, 0.005 equiv) was added to each vial, and the mixtures were stirred for 10 min. A 320 μL THF solution of M2 (8.00 mg, 28.5 μmol, 1.0 equiv) was added to vial B and, meanwhile, ethyl vinyl ether (100 μL) was added to vial A to quench the polymerization of M1. The mixture in vial B was stirred for another 10 min before ethyl vinyl ether (100 μL) was added. The mixture was stirred for 30 min. The polymer was purified with prep GPC before $^1$H NMR, GPC, and DSC characterization. 1H NMR (500 MHz, $CDCl_3$, ppm) δ 7.49-7.41 (m, 2H), 7.41-7.32 (m, 1H), 7.32-7.26 (m, 2H), 5.47-5.18 (m, 4H), 4.14-3.97 (m, 4H), 3.48-3.26 (m, 2H), 3.08-2.84 (m, 1H), 2.79-2.53 (m, 2H), 2.53-2.31 (m, 1H), 2.30-1.79 (m, 9H), 1.80-1.29 (m, 17H), 1.01-0.88 (m, 6H).

IIC. Polymerization Studies

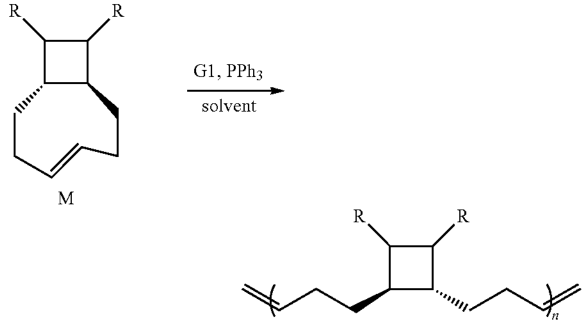

M (1) Introduction

Polymerization studies including the effects from various Ru initiators, monomer concentration, solvent, $[PPh_3]/[G1]$ ratio, [M]/[G1] ratio (Table 1) and monomer identity (Table 2), were performed. The studies were performed using G1 as the initiator in a $N_2$-filled glovebox. Stock solutions of M1, $PPh_3$ and G1 in THF were prepared in the glovebox. All vials and stir bars were dried in an oven overnight before being used for polymerization. The reaction was quenched with ethyl vinyl ether. The conversion for each entry was determined based on the integrations of olefinic $^1$H NMR peaks for monomer and polymer. The molecular weight and dispersity for each entry were measured by GPC.

TABLE 1

Polymerization study at 75/1 monomer/initiator ratio and varied $PPh_3$/G1 ratios

| M | Solvent | $[M]_o$ (M) | $[M]_o$/[G1] | $[PPh_3]$/[G1] | Conversion (%) | $M_{n, theo}$ (kDa) | $M_{n, GPC}$ (kDa) | Đ |
|---|---|---|---|---|---|---|---|---|
| M1 | THF | 0.05 | 75 | 30 | 100 | 25.2 | 23.8 | 1.17 |
| M1 | THF | 0.05 | 75 | 40 | 99 | 25.2 | 24.5 | 1.17 |
| M1 | THF | 0.05 | 75 | 50 | 100 | 25.2 | 25.1 | 1.17 |

TABLE 2

Polymerization study using different monomers

| M | Solvent | $[M]_o$ (M) | $[M]_o$/[G1] | $[PPh_3]$/[G1] | Conversion (%) | $M_{n, theo}$ (kDa) | $M_{n, GPC}$ (kDa) | Đ |
|---|---|---|---|---|---|---|---|---|
| M1 | THF | 0.25 | 400 | 60 | 97 | 134 | 156 | 1.23 |
| M2 | THF | 0.25 | 400 | 60 | 100 | 112 | 90 | 1.17 |
| M3 | THF | 0.25 | 400 | 60 | 97 | 101 | 93 | 1.16 |

(2) E/Z Ratio of Polymers

P2 from living ROMP was prepared using the procedure described above. P2 from equilibrium ROMP of ZM2 was prepared. The E/Z ratio could not be determined directly from the $^1$H NMR and $^{13}$C NMR of P2. The E/Z ratios were indirectly obtained from the trans/cis epoxide ratios in the completely epoxidized P2 as the stereochemistry is retained after epoxidation.

(3) Molecular Weight Control Study

Each polymerization was conducted at a monomer concentration of 0.05 M and $[PPh_3]/[G1]=30$. The [M1]/[G1] ratios were controlled to be 200, 400, 600, 800, 1000 and 1200. The polymerization was quenched at 10 min using ethyl vinyl ether and subjected to GPC analysis.

IID. Depolymerization Studies

All depolymerization studies were conducted in a $N_2$-filled glovebox. The depolymerization of P1 using G1 is shown below as an example:

Stock solutions of P1 and G1 in $CDCl_3$ were prepared. In an NMR tube was added P1 (8.40 mg, 25 μmol, 1.0 equiv), G1 (0.2057 mg, 0.25 μmol, 0.01 equiv). Additional $CDCl_3$ was added to reach a concentration of [olefin]=0.025 M. The mixture was left for 24 h. $^1$H NMR was performed to determine the percentage of depolymerization. GPC traces were collected to further confirm depolymerization.

IIE. Results and Discussion

Two common methods have been used to achieve olefin inversion. One uses a three-step sequence that involves epoxidation, formation of a β-hydroxy diphenylphosphine oxide, and elimination. This method is suitable for laboratory scale to prepare trans-cyclooctene. A drawback of this method is that the formation of β-hydroxy diphenylphosphine oxide requires the use of lithium diphenyl-phosphide, which is not compatible with electrophilic functional groups such as esters and imides. The second method involves photochemical isomerization in the presence of silver nitrate, which selectively binds to the trans-cycloalkene to form a water-soluble metal complex. The silver complex can be demetallated via washing with ammonium hydroxide to afford the trans-cycloalkene. Photochemical isomerization is compatible with a wide variety of functional groups, such as hydroxyl, esters, and imides, and advantageously requires only a single-step reaction. Conventional batch-type photoreaction of cyclooctene derivatives typically leads to low yields (<10%) due to the photodegradation of the trans-cyclooctene. To overcome this deficiency, the reaction mixture may continuously flow through a silver nitrate column; the trans-cyclooctene is selectively immobilized in the column, while its cis counterpart flows back to the photoreaction chamber for further reaction. Since a very low amount of trans-cyclooctene is exposed under ultraviolet light, its photodegradation is effectively minimized. This method is suitable for the cis-to-trans isomerization of cyclooctenes with various functional groups and gives a high yield in all cases (>60%). Synthesis of the E-alkene tCBCO monomers using this method resulted in M1 (33% yield), M2 (30% yield) and M3 (81% yield) from the photochemical isomerization of the Z-alkene monomers.

Trans-cyclooctene can undergo living ROMP in a condition where Grubbs first-generation catalyst (G1) was used as the initiator and an excess amount of triphenylphosphine ($PPh_3$) was added to suppress secondary metathesis. A coordinating solvent, such as tetrahydrofuran (THF), was found to be essential for a controlled polymerization. Since the tCBCO polymers are distinct from a regular polycyclooctene in that they can undergo depolymerization in the presence of a ruthenium catalyst.

Polymerization was tested using different ruthenium catalysts as the initiator, including the first-, second- and third-generation Grubbs catalysts (G1, G2 and G3) as well as the first- and second-generation Hoveyda-Grubbs catalysts (HG1 and HG2). In each case, 60 equiv $PPh_3$ were added with the initiator, and a control study without $PPh_3$ was also performed. M1 was used as the monomer, at a monomer/initiator ratio of 400 and an initial monomer concentration of 0.25 M. Each polymerization was quenched at 10 min by adding an excess amount of ethyl vinyl ether, and the resulting mixture was characterized with $^1$H NMR and GPC. When G2, G3 and HG2 were used as the initiator, significant fractions of ZM1 were detected from $^1$H NMR, indicating the occurrence of depolymerization through ring-closing metathesis. While low dispersities (D) were obtained with G3 and HG2 when 60 equiv $PPh_3$ were added, the fractions of depolymerization were 3%. Using G2 and HG1 as the initiator, regardless of adding $PPh_3$, led to polymers of high D (Table 3, entries 3, 4, 7, 8), which is likely due to their lower initiation rates compared to G1. In all cases, only G1 with 60 equiv $PPh_3$ (Table 1, entry 2) gave good molecular weight control accompanied by a low dispersity (D=1.18). In addition, the extent of depolymerization was suppressed to s 2%. This shows that the use of G1 and $PPh_3$, which was demonstrated to be able to effectively suppress secondary metathesis, can also suppress the depolymerization of the tCBCO polymers. G1 and excess $PPh_3$ were therefore used in the following polymerizations.

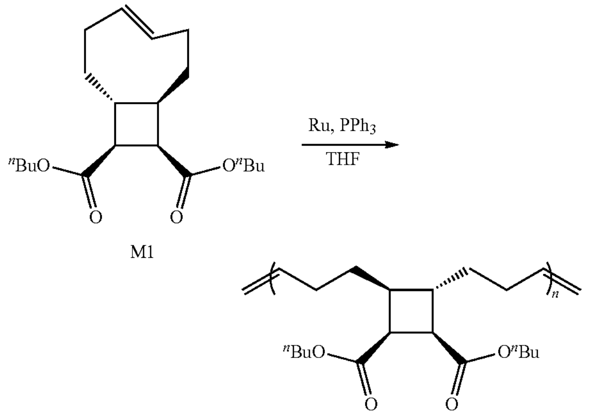

M1

P1

TABLE 3

| Initiator Screening | | | | | | |
|---|---|---|---|---|---|---|
| Entry | Ru | $PPh_3$/Ru | % P[b] | % ZM[c] | $M_{n, GPC}$ (kDa) [d] | Đ[e] |
| 1 | G1 | 0 | 95 | 1 | 571 | 2.14 |
| 2 | G1 | 60 | 97 | 2 | 175 | 1.18 |
| 3 | G2 | 0 | 17 | 19 | 882 | 1.68 |
| 4 | G2 | 60 | 5 | 2 | 303 | 1.76 |
| 5 | G3 | 0 | 47 | 51 | 1 | 1.30 |
| 6 | G3 | 60 | 16 | 3 | 29 | 1.09 |
| 7 | HG1 | 0 | 99 | 1 | 413 | 2.15 |
| 8 | HG1 | 60 | 96 | 2 | 12 | 1.30 |
| 9 | HG2 | 0 | 64 | 34 | 134 | 1.45 |
| 10 | HG2 | 60 | 21 | 6 | 26 | 1.13 |

M1 was used as the monomer, at a monomer/initiator ratio of 400; polymerization time was 10 min in each case and the reaction was quenched with ethyl vinyl ether. [b]Percentage of polymer in the polymerization mixture determined based on the integrations of olefinic $^1$H NMR peaks for ZM, M and polymer, same for following tables. [c]Percentage of ZM in the polymerization mixture determined from $^1$H NMR, same for following tables. [d]Number-average molecular weight measured by GPC in THF using polystyrene standards. [e]$M_w/M_n$, measured by GPC.

To examine the effect of elevated driving force enabled by monomer isomerization, the monomer concentration was screened to identify the limit for a successful and practical polymerization. It was found that when the initial monomer concentrations were ≥0.025 M, nearly quantitative (>97%) conversion, good agreement between measured number-average molecular weights ($M_n$) and the theoretical one, as well as narrow polydispersity (Đ≤1.2) were obtained in each case (Table 4, entries 11-15). Compared to the equilibrium ROMP of ZM, which requires a≥2 M monomer concentration to reach 80% conversion,[12] the low demand for monomer concentration of M would be particularly useful in situations where high concentrations are difficult to achieve, such as charged substrates or monomers with long side-chains. Further reduced concentrations (≤0.01 M, Table 4, entries 16-18) led to broadened dispersities (Đ≥1.3) accompanied by significant fractions of ZM1, indicating the occurrence of depolymerization through ring-closing metathesis.

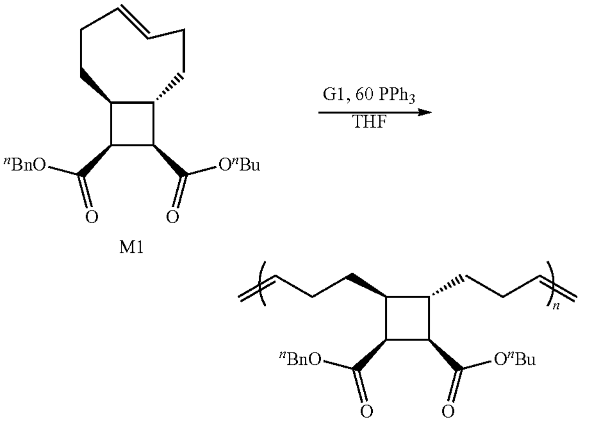

M1

P1

TABLE 4

| Concentration study for polymerization | | | | | | |
|---|---|---|---|---|---|---|
| Entry | $[M]_o$ (M) | % P | % ZM | $M_{n, theo}$ (kDa)[a] | $M_{n, GPC}$ (kDa) | Đ |
| 11 | 0.5 | 96 | 1 | 134 | 125 | 1.19 |
| 12 | 0.25 | 97 | 0 | 134 | 156 | 1.23 |
| 13 | 0.1 | 98 | 1 | 134 | 143 | 1.21 |
| 14 | 0.05 | 98 | 1 | 134 | 127 | 1.17 |
| 15 | 0.025 | 97 | 1 | 134 | 145 | 1.19 |
| 16 | 0.01 | 94 | 4 | 134 | 111 | 1.32 |
| 17 | 0.005 | 94 | 5 | 134 | 109 | 1.37 |
| 18 | 0.001 | 79 | 12 | 134 | 122 | 1.35 |

[a]Calculated based on $[M]_o$/[G1] ratio and the repeat unit molecular weight.

When the polymerization was conducted in dichloromethane, a lower conversion of 73% was obtained after 10 min, and the measured $M_n$ was significantly off from the theoretical value, suggesting that the coordination of THF indeed plays a critical role in controlling the polymerization. When a mixture of DCM and THF (1:1, v/v) was used as the solvent, the obtained $M_n$ matched well to the theoretical value. The permitted use of mixed solvents can be exploited for dissolving certain monomers or polymers that do not dissolve well in THF, therefore increasing the throughput of the method.

The $PPh_3$/G1 ratio was also varied. When ≥10 equiv $PPh_3$ was used, broad molecular weight distributions (Đ>1.35) were obtained. When 20 or higher equiv $PPh_3$ was used, the dispersity reduced to ~1.2. The excellent molecular weight control remained when a different monomer/initiator ratio (M1/G1=75) was used or different monomers (M2 and M3) were used.

Polymerization of the highly reactive M completed within 10 min, much shorter than the time required for the equilibrium ROMP of ZM (≥1 h). The polymerizations of M is under kinetic control, and therefore the alkene stereoselectivity differs from that of equilibrium ROMP of ZM, which is under thermodynamic control. The tCBCO polymers from the living ROMP of M2 and from the equilibrium ROMP of ZM2, and their trans/cis ratios were found to be 1.5 and 6.4, respectively.

The polymerization kinetics was studied at monomer concentration of 0.05 M and monomer to initiator ratio of 400/1, using G1 as the initiator with 30 equiv $PPh_3$.

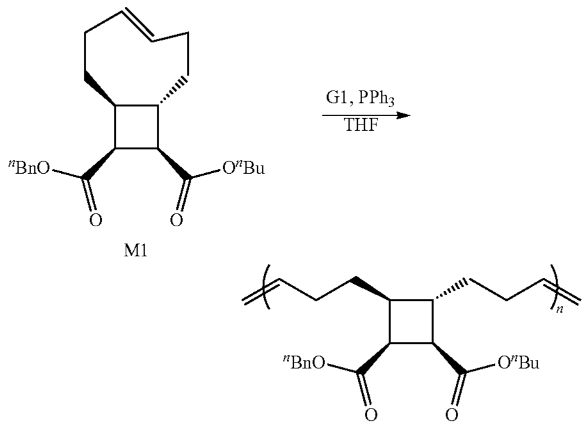

M1

P1

The polymerization reached over 90% conversion at 2 min. The living character of the polymerization is supported by the first-order kinetics as well as the linear relationship between $M_n$ and conversion. The plot of ln([M]o/[M]) versus time gave an observed rate constant of 0.0226 $s^{-1}$, corresponding to a propagation rate constant $k_p$=181 L $mol^{-1}$ $s^{-1}$. In addition, the $M_n$ at full conversion (10 min of polymerization) increased proportionally with $[M]_o$/[G1] ratio, further suggesting living polymerization. Notably, the excellent molecular weight control and the low Đ remained at $[M]_o$/[G1] ratio as high as 1200.

Due to the living nature of the polymerization, the viability of block copolymer synthesis was tested. M1 was allowed to polymerize for 10 min and the polymerization mixture was transferred to a THF solution of M2. The polymerization was allowed to proceed for another 10 min before being quenched with ethyl vinyl ether. The GPC traces suggest the formation of the block copolymer P1-b-P2. In addition, differential scanning calorimetry (DSC) curve of the resulting polymer showed two distinct glass transition temperatures ($T_g$) at −31° C. and 88° C., matching those of P1 ($T_g$=−31° C.) and P2 ($T_g$=92° C.), respectively, further supporting the formation of block copolymer. A well-known thermoplastic elastomer is the styrene-butadiene-styrene (SBS) rubber, which is an A-B-A type block copolymer of styrene and butadiene; the hard polystyrene blocks serve as the physical crosslinker while the soft polybutadiene block functions as the elastic segment. The capability of synthesizing block copolymers as well as accessing both low-$T_g$ and high-$T_g$ polymers demonstrated here provide an opportunity to prepare SBS like thermoplastic elastomer that can be chemically recycled.

The block copolymer P1-b-P2 underwent quantitative depolymerization to form a mixture of ZM1 and ZM2 when the polymer was dissolved in $CDCl_3$ ([olefin]=0.025 M) and stirred with 1 mol % G1 or G2 for 24 h. Kinetic studies of the depolymerization with G2 showed comparable depolymerization rates from the P1 and P2 blocks suggesting that the functional groups on the cyclobutane (i.e., ester and imide) do not significantly impact the depolymerization kinetics.

The high driving force provided by the high RSE of M and the suppression of depolymerization with $PPh_3$ are critical for the living ROMP at dilute conditions. Without $PPh_3$, a solution of P1 in $CDCl_3$ ([olefin]=0.025 M) was found to undergo nearly quantitative depolymerization (>95%) to form the cis-alkene monomer ZM1, when the polymer solution was stirred with 1 mol % G1 or G2 catalyst for 24 h under ambient conditions. When 60 equiv $PPh_3$ was added, no depolymerization was observed in the P1/G1/$PPh_3$ mixture whereas partial depolymerization was observed in the P1/G2/$PPh_3$ mixture. The absence of depolymerization in the condition of G1 with 60 equiv $PPh_3$ is consistent with the living polymerization condition in which excess $PPh_3$ suppresses secondary metathesis and depolymerization. On the other hand, excess $PPh_3$ could not completely shut down the secondary metathesis when G2 was used, suggesting that $PPh_3$ is less effective in reducing the reactivity of (IMes)Ru catalysts than it does to the ($PCy_3$)Ru catalysts. The ineffective suppression of G2 with $PPh_3$ is due to G2 binding preferentially to olefin over phosphine. The suppression effect of $PPh_3$ on G1 and G2 catalyzed depolymerization, was further investigated by varying the equivalence of $PPh_3$ relative to the ruthenium catalysts while keeping other conditions identical (i.e., [olefin]=0.025 M, 1 mol % Ru, ambient condition, and 24 h depolymerization time) and measured the extent of depolymerization accordingly. The trend that $PPh_3$ suppressed G1 catalyzed metathesis more effectively than it did to G2 catalyzed metathesis remained. For example, 5 equiv $PPh_3$ suppressed the depolymerization of P1/G1 mixture to 2% while only reduced the depolymerization of P2/G2 mixture to 86%. The more effective suppression of $PPh_3$ on G1 than it does to G2 was further supported by kinetic studies for depolymerization of P1 under the following four conditions: 1 mol % G1, 1 mol % G1 with 5 equiv $PPh_3$, 1 mol % G2, and 1 mol % G2 with 5 equiv $PPh_3$.

In summary, the cis-to-trans alkene isomerization of the tCBCO monomers enables the synthesis of depolymerizable polymers at a high driving force, allowing the polymerization to reach full conversion at monomer concentrations 2 orders of magnitude more dilute than the typical concentration for forming a depolymerizable polymer. Since the tCBCO polymers can depolymerize into the low-strain cis-alkene monomers, which can then be converted into the trans-alkene monomers through photochemical isomerization, the process of isomerization-polymerization-depolymerization therefore forms a closed loop that can be exploited for developing chemically recyclable polymers. The high-driving-force living ROMP makes it particularly convenient to synthesize tCBCO block copolymers by sequentially adding different monomers, which represents a rare case of fully depolymerizable block copolymers. The high driving force and the excellent functional group tolerance of the living ROMP of trans-alkene tCBCO monomers. In addition, the capability of $PPh_3$ to suppress secondary metathesis as well as the different levels of deactivation between G1 and G2 catalyzed systems could be leveraged to control material properties of dynamic covalent polymer networks that are based on olefin metathesis.

Example III

IIIA. Depolymerization Studies

Depolymerization experiments were performed with polymers P1, P2 and P3 at $[olefin]_o$=25 mM, 50 mM, 100 mM, 200 mM, and 400 mM. 1 mol % G2 was used for P1 and P2. With 1 mol % G2, we observed an unexpectedly low extent of depolymerization of P3, possibly due to the poisoning of the catalyst in presence of trace fluoroolefin impurities before equilibrium was reached. Thus, 2 mol % G2 was used for P3. Three parallel studies were conducted for each polymer at each concentration and the average extent of depolymerization was reported. Given below is a representative example of the depolymerization procedure.

In a 1-dram vial equipped with a stir bar, P1 (30 mg, 0.051 mmol, 1 eq.) was dissolved in 1990 μL $CHCl_3$. To the polymer solution was added G2 (0.43 mg, 0.00051 mmol, 0.01 eq.) in 10 μL $CHCl_3$ from a stock solution. The amount of the stock solution to be added was determined such that initial olefin concentration $[olefin]_o$=25 mM. The solution was divided into three vials and the depolymerization was allowed to progress overnight (~16 h) at room temperature following which 100 μL EVE was added to each vial. After stirring for 30 min., the solvent was removed via a rotary evaporator and the extent of depolymerization was determined by $^1H$ NMR.

IIIB. Water Contact Angle Measurements

To prepare the polymer surface for contact angle measurements, polymer solutions were prepared in solvents where the polymers can dissolve well. P3, P1-NF, and P2 were dissolved in toluene while P1 was dissolved in chloroform and P2-NF in chlorobenzene. 200 μL of a 5 wt. % solution of each polymer was loaded onto a glass plate mounted on the spin coater, which was then rotated at 2000 rpm for 60 seconds. Residual solvent was allowed to evaporate overnight under ambient conditions before the measurement.

The static contact angle was measured for a 10 μL water droplet deposited on the coated glass slides using a Rame-Hart contact angle goniometer. DROPImage advanced was used to calculate the contact angle from the droplet profile shape. For each sample, the measurement was taken immediately after addition of the droplet and was repeated six times, and the average value was reported.

IIIC. Self-Assembly of Amphiphilic Diblock Copolymer 3 mg of P1-b-P4 was dissolved in 0.3 mL THF and sealed in a microwave vial. To this, 3 mL MiliQ water was added dropwise over a span of 2 h via an automated syringe pump. The solution was then dialyzed with DI water for 36 h (MW cutoff for dialysis tubing: 12 kDa), following which it was filtered with a 0.22 μm PTFE filter and stored at room temperature. Particle size of the micelles was measured via dynamic light scattering.

IIID. Para-Fluoro-Thiol $S_NAr$ Reaction

In a 1-dram vial equipped with a stir bar, was dissolved P2 (10 mg, 0.026 mmol, 1 eq.) in 2-butanone (200 μL). To the polymer solution were added thiophenol (3.01 mg, 0.027 mmol, 1.05 eq.) and $K_2CO_3$ (5-4 mg, 0.039 mmol, 1.5 eq.). The vial was placed in a preheated oil bath at 80° C. and allowed to stir for 4.5 h, after which the reaction mixture was filtered through a celite plug, and the filtrate was concentrated on a rotavap. After further drying under high vacuum, the product was analyzed vial $^{19}F$ NMR and GPC.

IIIE. Synthesis (1) Small Molecule Synthesis

M1

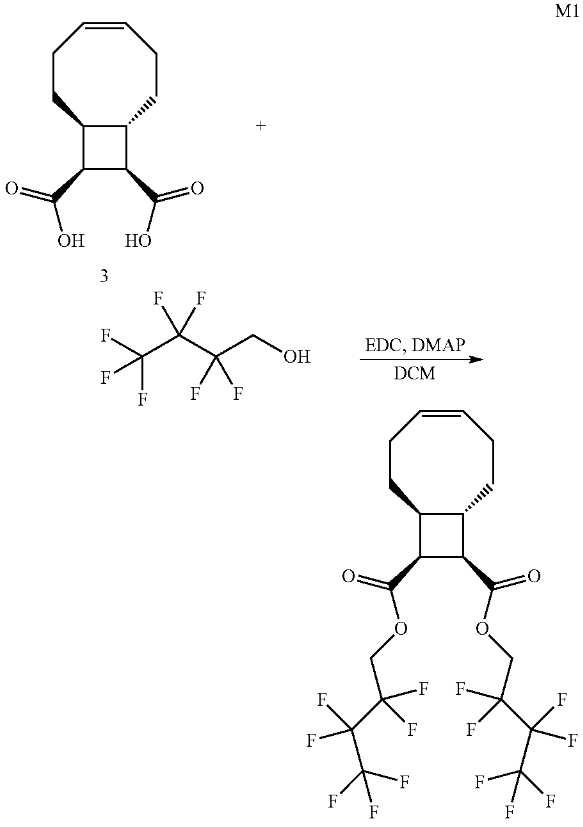

3

M1

To a round bottom flask equipped with astir bar were added 3 (0.772 g, 3-45 mmol, 1 eq.) (prepared according to literature procedure)[2], 2,2,3,3,4,4,4-heptafluoro-1-butanol (0.94 mL, 7.25 mmol, 2.1 eq.), N,N-dimethylaminopyridine (0.084 g, 0.69 mmol, 0.2 eq.) and DCM (25 mL). To this solution was added EDC (2.639 g, 13.8 mmol, 4 eq.). The reaction was then allowed to continue overnight at room temperature. The reaction mixture was diluted with DCM, washed with brine (×3), and concentrated on a rotavap. The residue was purified via column chromatography with 5% EA/hexanes as eluent, affording M1 as a colorless oil. Yield: 1.34 g (66.2%). $^1H$ NMR (500 MHz, $CDCl_3$, ppm): δ 5.70-5.57 (m, 2H), 4.64-4.47 (m, 4H), 3.54-3.51 (m, 1H), 2.88-2.84 (m, 2H), 2.55-2.49 (m, 1H), 2.28-2.12 (m, 1H), 2.29-2.02 (m, 5H), 1.67-1.61 (m, 1H), 1.30-1.20 (m, 2H); $^{19}F$ NMR (470 MHz, $CDCl_3$, ppm): δ −81.00 (dt, J=19.1 Hz, 9.2 Hz, 6F), −120.45--120.64 (m, 4F), −127.62--127.74 (m, 4F); $^{13}C$ NMR (125 MHz, $CDCl_3$, ppm): δ 171.14, 170.47, 130-52, 129.61, 118.66, 116.37, 113.93, 111.89, 110.82, 108.73, 106.64, 59.46, 43.29, 42.28, 42.04, 39.53, 34.14, 28.79, 24.13, 23.47. HRMS-ESI (m/z): calcd. for $C_{20}H_{18}F_{14}NaO_4^+$ [M+Na]$^+$, 611.0874; found, 611.0918.

E-M1

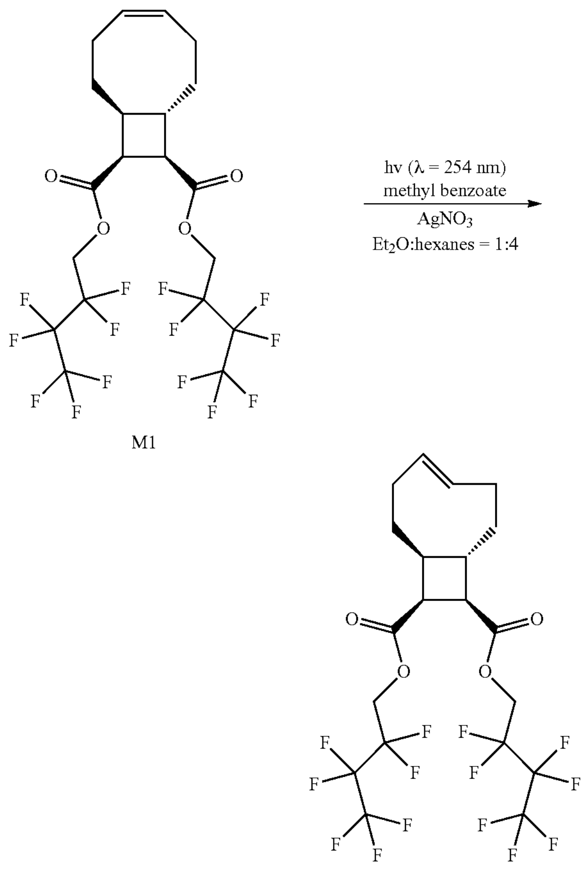

M1

E-M1

The photoisomerization was conducted according to the procedures described above. M1 (235 mg, 0.4 mmol, 1.0 equiv) and methyl benzoate (109 mg, 0.8 mmol, 2.0 equiv) were dissolved in a 1:4 v/v $Et_2O$/hexane solvent mixture in a quartz tube. A column was first filled with a small amount of normal silica gel at the bottom to prevent silver leaking and then filled with 10 wt % $AgNO_3$-impregnated silica gel (136 mg $AgNO_3$, 0.8 mmol, 2.0 equiv). The reaction mixture was irradiated overnight with 254 nm UV light in a Rayonet photoreaction chamber with 16 RPR-2537A lamps, and meanwhile, it was circulated through the above-mentioned column using a metering pump. All substances in the column were loaded to a column packed with normal silica gel and $AgNO_3$-impregnated silica gel. The column was washed with 1:4 v/v $Et_2O$/hexanes to remove M1 and methyl benzoate. Acetone was then used to wash the column to elute out $Ag^+$ coordinated E-M1. After the removal of acetone using rotary evaporator, DCM and aqueous ammonia solution were added, and the mixture was stirred for 30 min. The organic phase was collected, and the aqueous phase was further extracted with DCM for 3 times. The combined organic phase was washed with water and brine and dried over sodium sulfate. After filtration and removal of solvent, the resulting yellow oil was run through a short plug of silica gel, affording a white solid as the product (127 mg, yield=54%). The product contained a mixture of two diastereomers and was used without further separation. $^1$H NMR (500 MHz, $CDCl_3$, ppm): δ 5.87-5.73 (m, 0.4H), 5.56-5.43 (m, 1.6H), 4.65-4.39 (m, 4H), 3.51 (t, J=9.1 Hz, 0.8H), 3.48-3.43 (m, 0.2H), 2.62-2.34 (m, 1.2H), 2.33-1.90 (m, 5.8H), 2.43-1.88 (m, 4H), 1.58-1.48 (m, 2H); $^{19}$F NMR (470 MHz, $CDCl_3$, ppm): δ −81.01 (dt, J=25.6 Hz, 9.2 Hz, 6F), −120.48--120.66 (m, 4F), −127.67--127.73 (m, 4F); $^{13}$C NMR (125 MHz, $CDCl_3$, ppm): δ 171.1, 170.9, 170.3, 170.2, 136.6, 134.9, 134.4, 134.2, 118.6, 116.3, 113.9, 113.8, 111.8, 108.5, 59.6, 59.5, 59.4, 59.3, 59.2, 59.1, 46.4, 45.4, 44.6, 44.0, 43.2, 43.0, 42.4, 41.4, 40.9, 40.3, 35.7, 35.5, 33.0, 32.7, 25.7, 25-4. HRMS-ESI (m/z): calcd. for $C_{20}H_{18}F_{14}NaO_4^+$ [M+Na]$^+$, 611.0874; found, 611.0811.

M2

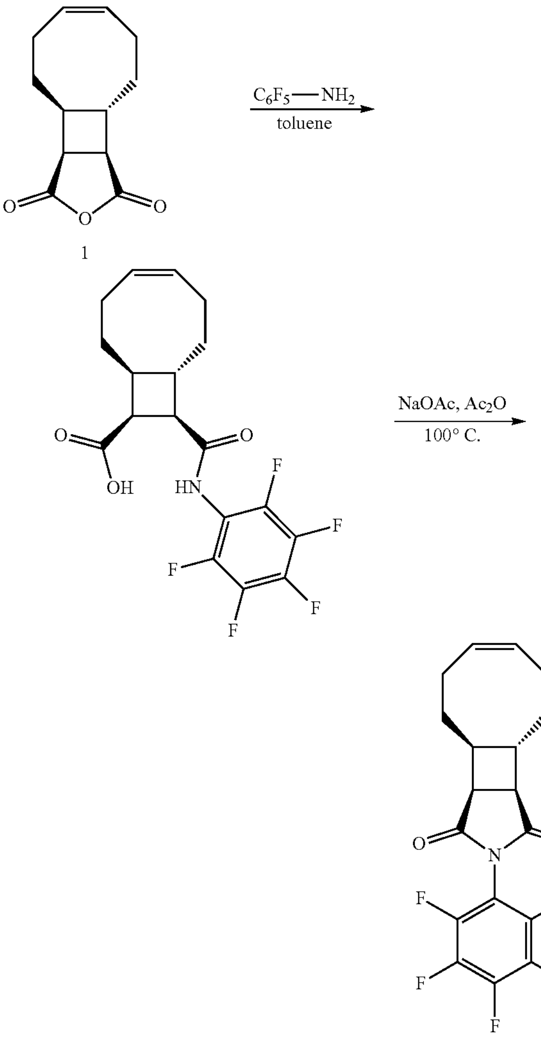

M2

Anhydride 1 (0.92 g, 4.46 mmol, 1 eq.) and 2,3,4,5,6-pentafluoroaniline (1.68 g, 9.2 mmol, 2.06 eq.) were dissolved in toluene (10 mL), and the solution was heated at 90° C. overnight, during which an off-white precipitate emerged. The precipitate was filtered and dried to afford the amic-acid intermediate, which was used for the next step without further purification. The amic-acid (726 mg, 1.87 mmol, 1 eq.) was then added into a round bottom flask together with sodium acetate (240 mg, 2.92 mmol, 1.6 eq.) and acetic anhydride (10 mL). The mixture was heated at 100° C. overnight, and then poured into cold water and stirred for 30 min. The resulting precipitate was filtered and purified via column chromatography using DCM to afford pure monomer M2. Yield: 546 mg (~78.9%). $^1$H NMR (500 MHz, $CDCl_3$, ppm): δ 5.68-5.60 (m, 2H), 3.48-3.45 (m, 1H), 3.11 (t, J=6.4 Hz, 1H), 2.86-2.79 (m, 1H), 2.57-2.50 (m, 1H), 2.33-2.25 (m, 1H), 2.24-2.19 (m, 1H), 2.16-2.08 (m, 2H), 2.07-2.01 (m, 1H) 1.92-1.86 (m, 1H), 1.65-1.58 (m, 1H), 1.43-1.36 (m, 1H). $^{19}$F NMR (470 MHz, $CDCl_3$, ppm): δ −142.9 (dtd, J=22.0, 6.5, 2.1 Hz, 1F), −143.6 (dtd, J=23.0, 6.5, 2.2 Hz, 1F), −152.1--152.2 (m, 1F), −160.7--160.8 (m, 1F), −161.0--161.1 (m, 1F) $^{13}$C NMR (125 MHz, $CDCl_3$, ppm): δ 175.98, 174.70, 144.67, 143.17, 142.36, 141.12, 138.89, 137.04, 136.92, 130.09, 129.75, 45.64, 42.41, 40.56, 40.34, 32.80, 29.25, 23.97, 23.81 HRMS-ESI (m/z): calcd for $C_{18}H_{15}F_5NO_2^+$ $[M+H]^+$, 372.1017; found, 372.1061.

M3

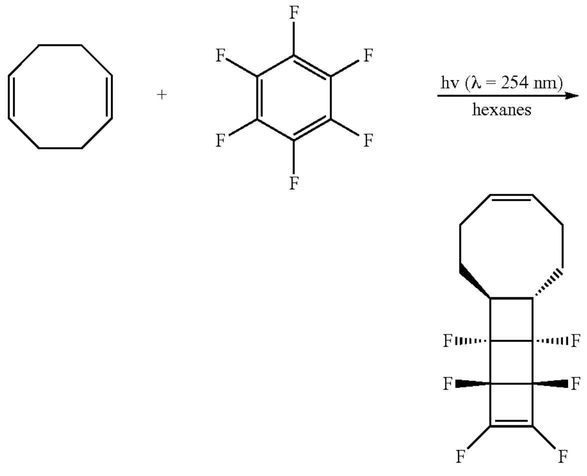

M3

To an oven-dried quartz flask was added a solution of cyclooctadiene (1.32 mL, 10.75 mmol, 1.0 equiv.) and hexafluorobenzene (1.24 mL, 10.75 mmol, 1.0 equiv.) in 100 mL hexanes. The reaction mixture was bubbled with $N_2$ for 30 min and then irradiated with 254 nm UV light in a Rayonet photoreaction chamber with 16 RPR-2537A lamps for 24 h. The mixture was washed with sat. $NaHCO_3$ (a.q.), extracted with hexanes and dried with $Na_2SO_4$. After filtration and solvent removal, the crude product was purified by column chromatography with hexanes as the eluent to obtain 1.01 g product as a colorless oil (yield: 31.8%, containing 5~7% of cis-isomer, when the reaction concentration was increased, the amount of cis-isomer was increased). The product was polymerized by using 1 mol % G2 as initiator at 1 g/mL concentration in DCM and quenched with EVE. The polymerization solution was then precipitated in MeOH to obtain a white fibrous polymer. After drying on vacuum overnight, the polymer was depolymerized in $CHCl_3$ ($[olefin]_o$=0.1 M) in the presence of 1 mol % G2 at 50° C. for 2 h and quenched with EVE. The pure trans-isomer was separated through flash column chromatography from the depolymerization mixture. $^1$H NMR (500 MHz, $CDCl_3$, ppm): δ 5.76-5.61 (m, 2H), 2.93-2.79 (m, 1H), 2.72-2.61 (m, 1H), 2.43-2.32 (m, 1H), 2.26-2.09 (m, 3H), 1.95-1.86 (m, 1H), 1.84-1.67 (m, 3H); $^{19}$F NMR (470 MHz, $CDCl_3$, ppm): δ −120.00 (tt, J=11.6, 5.4 Hz), −120.46 (td, J=11.6, 5.8 Hz), −154.06 (dddd, J=24.1, 15.9, 12.2, 4.1 Hz), −182.14, −186.53 (qd, J=10.6, 9.9, 4.8 Hz), −186.75 (ddt, J=16.8, 11.0, 4.9 Hz); $^{13}$C NMR (125 MHz, $CDCl_3$, ppm): δ 130.8, 130.3, 130.2, 130.1, 100.9, 100.3, 95.6, 94.5, 47.4, 37.1, 26.3, 25.3, 25.0, 22.9. HMRS (ASAP) calcd. for $C_{14}H_{12}F_6^-$ $[M]^-$ 294.0849, found 294.0822.

Fluorinated Ladderane Epoxide 2

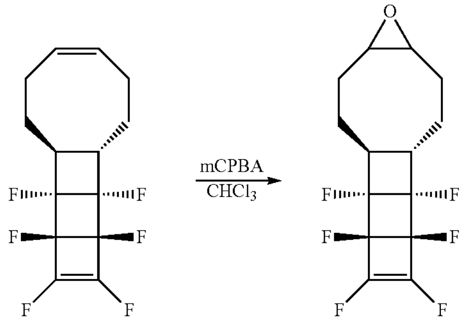

M3 2

To around bottom flask was added a solution of M3 (0.16 g, 0.53 mmol, 1.0 equiv.) in 5 mL $CHCl_3$, and the solution was cooled down in an ice bath. A solution of mCPBA (0.12 g, 0.53 mmol, 1.0 equiv. 75 wt %) in 5 mL $CHCl_3$ was added dropwise into the solution of M3. The reaction mixture was allowed to stir overnight and slowly warm to room temperature. The mixture was washed with sat. $NaHSO_3$ (a.q.) and sat. $NaHCO_3$ (a.q.), extracted with DCM and dried over $Na_2SO_4$. After filtration and concentration, the crude product was purified by column chromatography, affording 0.12 g product as a white solid (yield: 73.8%). $^1$H NMR (500 MHz, $CDCl_3$, ppm): δ 3.06-2.83 (m, 2H), 2.70-2.16 (m, 4H), 2.10-1.80 (m, 3H), 1.79-1.60 (m, 1H), 1.47-1.09 (m, 2H); $^{19}$F NMR (470 MHz, $CDCl_3$, ppm): δ −119.6--119.9 (m), −120.0--120.2 (m), −153.3--154.2 (m), −182.4--184.8 (m), −185.7--187.2 (m); $^{13}$C NMR (125 MHz, $CDCl_3$, ppm): δ 130.8, 130.2, 101.2, 100.0, 95.8, 94.6, 54.7 (3C), 54.6 (3C), 48.0, 47.3, 37.6, 37.4, 27.8, 26.9, 24.0, 23.7, 23.6, 22.1, 21.7, 21.5. HMRS (ASAP) calcd. for $C_{14}H_{12}F_6^-$ $[M]^-$ 310.0792, found 310.0802.

Compound 6

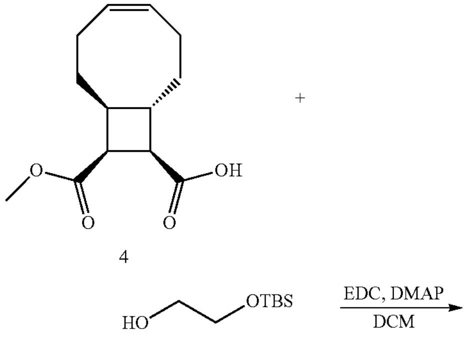

4

5

-continued

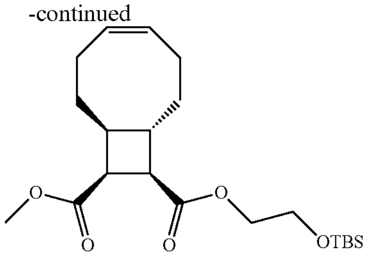

6

To a 250 mL round bottom flask equipped with a stir bar were added 4 (3727.6 mg, 15.6 mmol, 1 eq.), 5 (3030.7 mg, 17.2 mmol, 1.1 eq.), N,N-dimethylaminopyridine (191.1 mg, 1.56 mmol, 0.1 eq.), EDC (6000 mg, 30.3 mmol, 2 eq.), and DCM (80 mL). The reaction was allowed to continue for 18 h at room temperature, following which it was diluted with DCM, washed with water (2×200 mL), and concentrated on a rotavap. After column chromatography with 8% EA/hexanes as eluent, 6 was obtained as a pale-yellow oil. Yield: 3.85 g (62%). $^1$H NMR (500 MHz, $CDCl_3$, ppm): δ 5.68-5.54 (m, 2H), 4.13 (td, J=5.1 Hz, 3.1 Hz, 2H), 3.82-3.75 (m, 2H), 3.65 (s, 3H), 3.39 (t, J=10 Hz, 1H), 2.82 (qd, J=10.5 Hz, 4.5 Hz, H), 2.70-2.67 (m, 1H), 2.43-2.36 (m, 1H), 2.27-2.20 (m, 1H), 2.19-2.11 (m, 2H), 2.07-2.00 (m, 2H), 1.64-1.57 (m, 1H), 1.32-1.25 (m, 1H), 1.24-1.17 (m, 1H), 0.9 (s, 9H), 0.07 (s, 6H). $^{13}$C NMR (125 MHz, $CDCl_3$, ppm): δ 173.09, 172.74, 130.58, 129.76, 63.75, 63.15, 51.37, 43.71, 42.82, 42.00, 39.21, 34.48, 28.99, 25.83, 24.39, 23.67, 18.29, 5.34. calcd. for $C_{21}H_{36}NaO_5Si^+$ $[M+Na]^+$: 419.2224; found: 419.2206.

Compound E-6

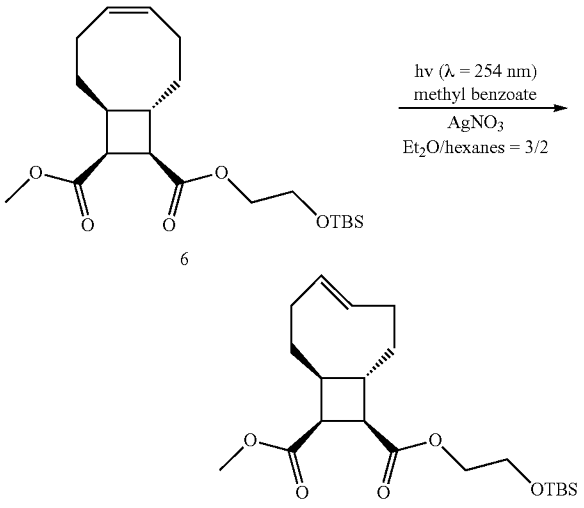

6

E-6

The photoisomerization of 6 was performed followed by dissolving 6 (3.85 g, 9.71 mmol, 1 eq.) and methyl benzoate (1.32 g, 9.71 mmol, 1 eq.) in a 150 mL of 3:2 v/v $Et_2O$/hexanes solvent mixture in a quartz tube. First, a column was filled with a small amount of normal silica gel at the bottom to prevent silver leaking and then filled with 10 wt % $AgNO_3$-impregnated silica gel (3.3 g $AgNO_3$, 19.4 mmol, 2 eq.). The reaction mixture was irradiated overnight with 254 nm UV light in a Rayonet photoreaction chamber with 16 RPR2537A lamps, and meanwhile, it was circulated through the column using a metering pump. After 17 h of irradiation, the contents of the column were collected and loaded onto another column with a normal silica gel layer at the bottom, and a fresh $AgNO_3$-impregnated silica gel layer (3.3 g AgNO3, 19.4 mmol, 2 eq.) at the top. First, 6 and methyl benzoate were eluted from the column using 750 mL of 3:2 v/v $Et_2O$/hexanes as eluent. Further, acetone was used to elute out the $Ag^+$ coordinated E-6. Acetone was removed via a rotary evaporator, and 50% aq. $NH_4OH$ was added to the residue. The mixture was added to a separatory funnel and the aqueous layer was extracted with DCM (5×300 mL), dried over $Na_2SO_4$, filtered, and concentrated on a rotavap. The brown crude oil was purified via column chromatography using 8% EA/hexanes mixture as the eluent. After solvent removal, the product E-6 was obtained as a pale-yellow oil. The product contained a mixture of 2 diastereomers and was used without further purification. Yield: 2.25 g (58%). $^1$H NMR (500 MHz, $CDCl_3$, ppm): δ 5.86-5.73 (m, 0.5H), 5.53-5.46 (m, 1.5H), 4.15-4.08 (m, 2H), 3.81-3.76 (m, 2H), 3.63 (s, 3H), 3.38 (t, J=9.1 Hz, 0.75H), 3.31 (t, J=8.7 Hz, 0.25H), 2.75-2.68 (m, 0.25H), 2.65-2.51 (m, 1.75H), 2.4-1.89 (m, 6H), 1.86-1.75 (m, 1H), 1.70-1.58 (m, 1H), 1.58-1.47 (m, 1H), 0.9 (s, 9H), 0.07 (s, 6H). $^{13}$C (125 MHz, $CDCl_3$, ppm): 173.0, 172.8, 134.5, 134.4, 65.8, 61.1, 51.4, 45.3, 43.7, 42.8, 41.2, 35.7, 33.2, 33.0, 25.8, 18.3, −5.3. calcd. for $C_{21}H_{36}NaO_5Si^+$ $[M+Na]^+$: 419.2224, found: 419.2192.

Compound E-7

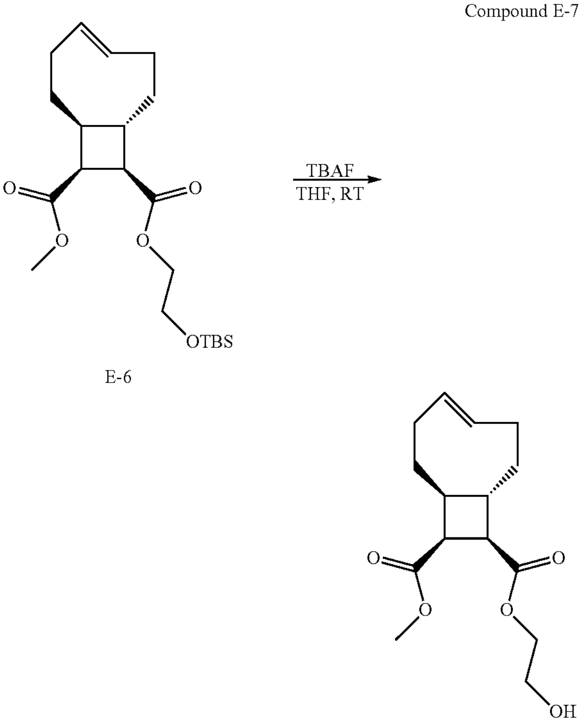

E-6

E-7

The desilylation of the photoisomerization product was carried out in the presence of a fluoride instead of a strong Brønsted acid (e.g. HCl), can lead to hydration of the olefin in trans-cyclooctene. To a solution of the silyl ether E-6 (2.25 g, 5.67 mmol) in THF (5.67 mL) was added TBAF (1 M solution in THF, 11.2 mL, 11.2 mmol, 2 eq.). The mixture was stirred at ambient conditions for 30 min, at which point TLC (1:1 v/v EA/hexanes) suggested full conversion. The reaction mixture was then diluted with EA, washed with D.I. $H_2O$ three times and brine, and dried over $Na_2SO_4$. The solution was concentrated and directly loaded on a silica column. Flash column chromatography (EA/hexanes=1:1) yielded a slightly yellow oil (1282 mg, 80%). The non-solid product was kept in a dilute solution with a known amount of BHT to prevent radical-induced side reactions on trans-cyclooctene and as internal reference for mass calculation. $^1H$ NMR (500 MHz, $CDCl_3$, ppm): δ 5.86-5.74 (m, 0.25H), 5.53-5.46 (m, 1.75H), 4.25-4.16 (m, 2H), 3.84-3.75 (m, 2H), 3.66 (s, 3H), 3.38 (td, J=9.2, 0.9, Hz, 0.87H), 3.35 (t, J=8.6 Hz, 0.13H), 2.74-2.62 (m, 1H), 2.58-2.52 (m, 1H), 2.39-1.99 (m, 6H), 1.82-1.79 (m, 1H), 1.69-1.59 (m, 1H), 1.56-1.49 (m, 1H); $^{13}C$ (125 MHz, $CDCl_3$, ppm): 173.8, 172.7, 136.6, 135.0, 134.4, 134.4, 66.2, 65.8, 61.1, 51.6, 50.8, 46.4, 45.5, 45.3, 44.0, 43.6, 43.1, 43.0, 42.6, 42.1, 41.1, 40.4, 39.1, 36.1, 35.8, 33.2, 32.9, 15.2, 14.2 calcd. for $C_{15}H_{22}NaO_5^+$ $[M+Na]^+$: 305.1357, found: 305.1378.

Compound 8

PEG succinate ester 7

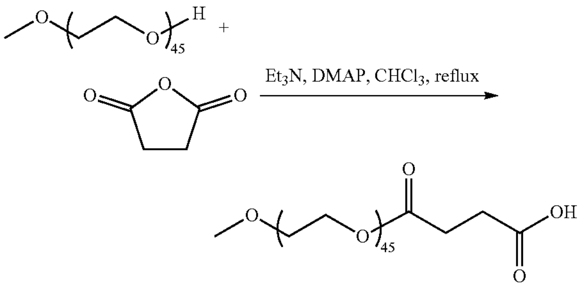

8

Following reported procedures with slight modifications, mPEG (3.8 g, 1.9 mmol, 1 eq.), succinic anhydride (0.95 g, 9.5 mmol, 5 eq.), $Et_3N$ (0.96 g, 9.5 mmol, 5 eq.) and DMAP (232 mg, 1.9 mmol, 1 eq.) were dissolved in chloroform (amylene stabilized) and left to reflux for 24 h. The mixture was concentrated on a rotary evaporator and was redissolved in 1 N HCl. The aqueous solution was washed with 1:1 v/v EA/hexanes (3×) and extracted with DCM three times. The DCM solution was dried over $Na_2SO_4$, concentrated to around 10% (w/v) and precipitated into cold $Et_2O$ (2×), affording a white powder. $^1H$ NMR (500 MHz, $CDCl_3$, ppm): δ 4.27-4.25 (m, 2H), 4.68-3.64-4.25 (m, 178H), 3.38 (s, 3H), 2.68-2.61 (m, 4H).

E-M4

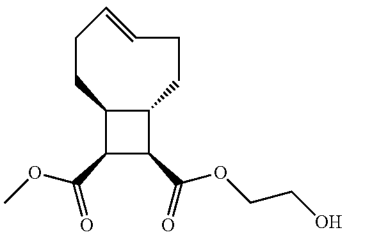

E-7

+

-continued

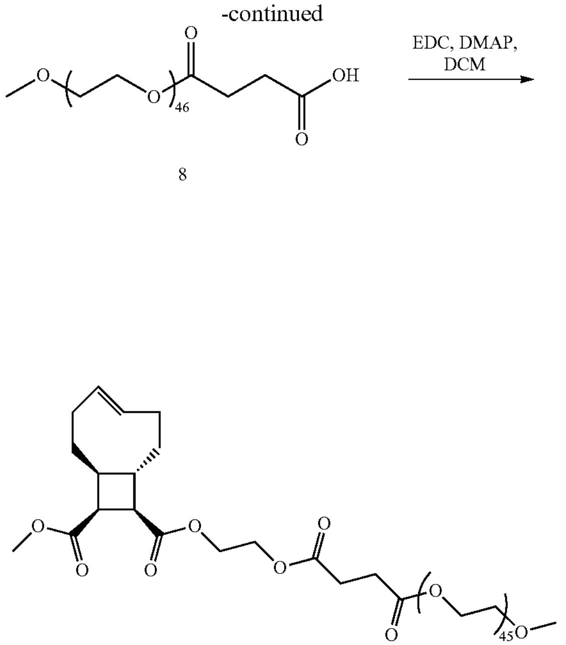

8

E-M4

To a 25 mL round-bottom flask equipped with a stir bar were added E-7 (100 mg, 0.35 mmol, 1.2 eq.), DMAP (3.7 mg, 0.035 mmol, 0.1 eq.), PEG succinate ester 8 (618 mg, 0.3 mmol, 1 eq.), EDC (115 mg, 0.6 mmol, 2 eq.), and DCM (10 mL), and the reaction mixture was allowed to stir at room temperature overnight. The mixture was concentrated at a reduced pressure before 150 mL D.I. $H_2O$ was added. The aqueous layer was washed with 1:1 v/v EA/hexanes mixture (3×200 mL), and the organic layer was discarded. The aqueous layer was extracted with DCM (6×200 mL). The combined organic layer was dried over $Na_2SO_4$, filtered, and concentrated at a reduced pressure, and then precipitated into cold $Et_2O$ (×2). The product was obtained as a white solid (475 mg, yield: 67%). $^1H$ NMR (500 MHz, $CDCl_3$, ppm): δ 5.85-5.74 (m, 0.5H), 5.52-5.45 (m, 1-5H), 4.29-4.23 (m, 6H), 3.64 (s, 183H), 3.4-3.32 (m, 4H), 2.82-2.49 (m, 6H), 2.41-1.47 (m, 9H).

(2) Polymer Synthesis

P1

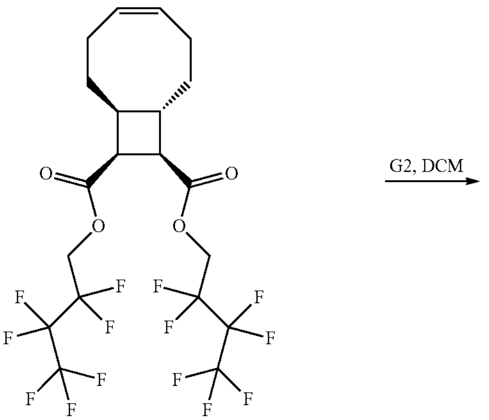

M1

-continued

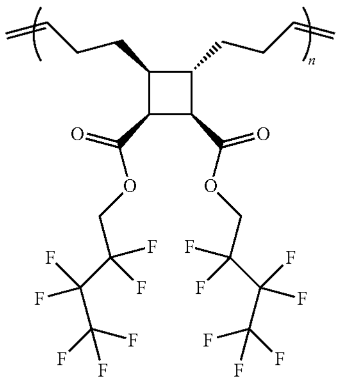

P1

To a 1-dram vial equipped with a stir bar, were added M1 (250 mg, 0.42 mmol, 1 eq.) and DCM (30 μL). To the monomer solution was added G2 (0.72 mg, 0.00085 mmol, 0.002 eq.) in 20 μL DCM from a stock solution. The polymerization was allowed to continue overnight at room temperature. The reaction was quenched with ethyl vinyl ether (100 μL) and stirred for 30 min. To the mixture Quadrapure TU microporous particles (100 mg) and DCM (1 mL) were added. The mixture was stirred for 12 h and was then filtered through a celite plug and concentrated. Pure polymer was obtained by precipitation in hexanes (×3). Yield: 110 mg (~44%). $M_n$=276 kDa, D=1.42. $^1$H NMR (500 MHz, $CDCl_3$, ppm): δ 5.41-5.29 (m, 2H), 4.61-4.65 (m, 4H), 3.57 (t, 1H), 2.91-2.86 (s, 1H), 2.72-2.66 (m, 1H), 2.77-2.73 (m, 1H), 2.23-2.16 (m, 1H), 2.05-1.91 (m, 4H), 1.55-1.46 (m, 4H); $^{19}$F NMR (470 MHz, $CDCl_3$, ppm): δ −81.17 (m, 4F), −120.72 (m, 2F), −127.84 (m, 2F).

P2

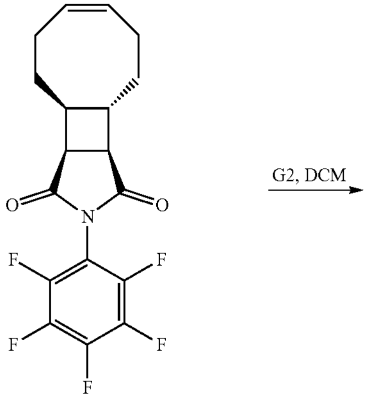

M2

-continued

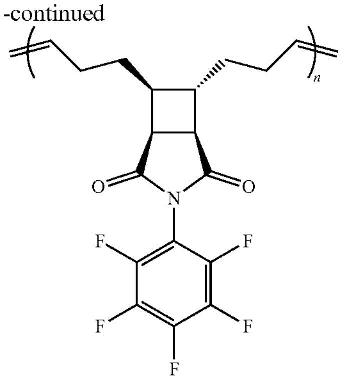

P2

To a 1-dram vial equipped with a stir bar, was added M2 (0.3 g, 0.81 mmol, 1 eq.) and DCM (300 μL). To the monomer solution was added a solution of G2 (1.37 mg, 0.00162 mmol, 0.002 eq.) in (20 μL) DCM from a stock solution, and the polymerization was allowed to continue overnight at room temperature. It was quenched with ethyl vinyl ether (100 μL), and after stirring for 30 min., Quadrapure TU microporous particles (250 mg) and DCM (1 mL) were added. The mixture was stirred for 12 h, following which it was filtered through a celite plug and concentrated. Pure polymer was obtained by precipitation in methanol (×3). Yield: 0.22 g (~73%). $M_n$=147 kDa, D=1.75. $^1$H NMR (500 MHz, $CDCl_3$, ppm): δ 5.44-5.33 (m, 2H), 3.55-3.50 (m, 1H), 3.06 (t, 1H), 2.51-2.46 (m, 1H), 2.23 (m, 1H), 2.09-2.04 (m, 4H), 1.74-1.64 (m, 3H), 1.47 (s, 1H). $^{19}$F NMR (470 MHz, $CDCl_3$, ppm): δ −143.12 (2F, ortho), −151.1 (1F, para), −160.86 (2F, meta).

P3

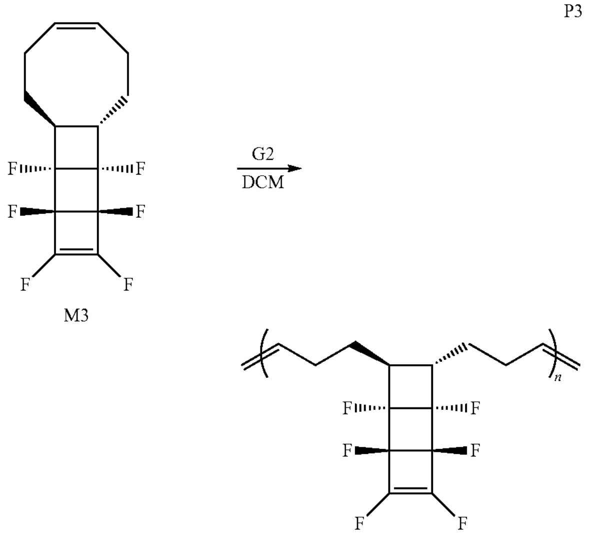

M3

P3

To a 1-dram vial was added M3 (0.50 g, 1.70 mmol, 1.0 equiv.). G2 (2.89 mg, 3.40 mmol, 0.002 equiv.) was weighed in another vial and dissolved in 0.85 mL DCM, and the solution was added to the vial containing the monomer. The reaction mixture was allowed to stir at room temperature overnight. The polymerization was then quenched with 1.0 mL ethyl vinyl ether and stirred for 30 min, at which point, Quadrapure TU macroporous particles (150 mg) and 2.0 mL DCM were added. The mixture was stirred for 5 h, filtered through a Celite plug and concentrated under reduced pressure. The concentrated solution was precipitated in 200 mL cold methanol for three times and dried on vacuum, yielding P3 as white fibers. Yield: 0.30 g (60%). $M_n$=108.3 kDa, Đ=1.63. $^1$H NMR (500 MHz, $CDCl_3$, ppm): δ 5.50-5.33 (m, 2H), 2.68-2.52 (m, 1H), 2.47-2.37 (m, 1H), 2.16-1.97 (m, 4H), 1.89-1.74 (m, 2H), 1.75-1.64 (m, 1H), 1.64-1.54 (m, 1H); $^{19}$F NMR (470 MHz, $CDCl_3$, ppm): δ −120.2 (2F), −153.0, −184.0, −186.9 (d, J=85.1 Hz), −187.8.
P1-b-P4
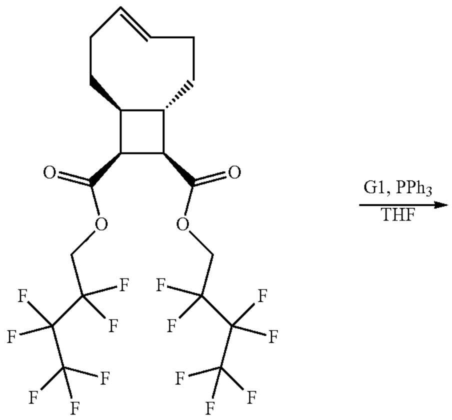
E-M1
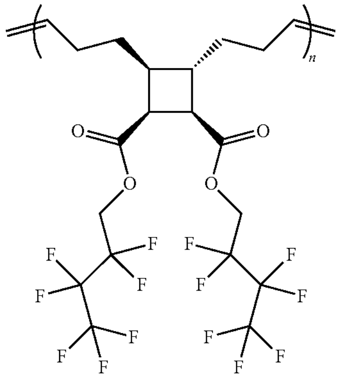
P1
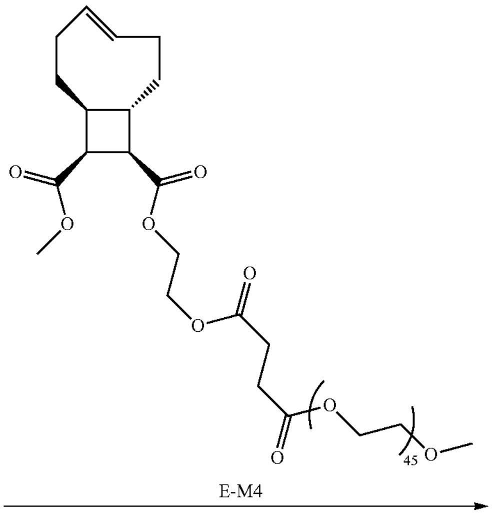
E-M4

-continued

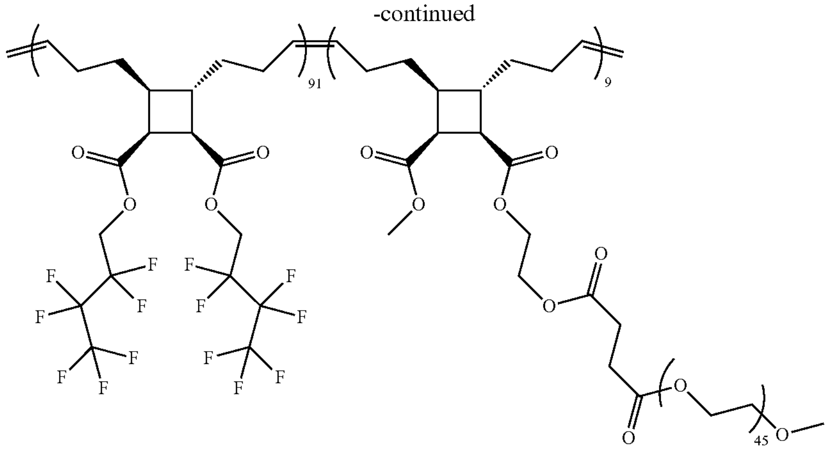

P1-b-P4

To a vial were added E-M1 (58.8 mg, 100 μmol, 1.0 equiv) and $PPh_3$ (7.89 mg, 30 μmol, 0.3 equiv). THF was added to reach a monomer concentration of 0.25 M. G1 (0.82296 mg, 1 μmol, 0.01 equiv) was added while vigorous stirring, and the mixture was stirred for 10 min. An aliquot was taken at this point for analysis of the first block. To the polymerization mixture was added 900 μL THF solution of E-M4 (23.59 mg, 10 μmol, 0.1 equiv). The mixture was stirred for another 10 min before ethyl vinyl ether (1 mL) was added. After stirring for 30 min, solvent was removed under reduced pressure, and the polymer was purified with a prep GPC. The ratio of DP for the two blocks was determined to be approximately P1:P4=91.2:8.8 from the integral at 4.67-4.40 (4H for P1) and 4.40-4.16 (6H for P2) in the $^1H$ NMR. The GPC trace of the first block (P1) showed $M_n$=42.2 kDa and Đ=1.08. However, the GPC trace obtained after synthesis of the second block showed a higher retention time (lower $M_n$) than the first block, precluding the accurate determination of the M. of P1-b-P4 (FIG. S41). We therefore used the $M_n$ obtained from the GPC trace of the first block and the ratio of the two blocks obtained from NMR to estimate the $M_n$. $M_n$=58.5 kDa. $^1H$ NMR (500 MHz, $CDCl_3$, ppm) δ 5.49-5.15 (m, 200H), 4.67-4.40 (m, 364H), 4.40-4.16 (m, 54H), 3.81-3.60 (m, 1629H), 3.59-3.52 (m, 100H), 2.94-2.73 (m, 100H), 2.73-2.58 (m, 136H), 2.26-2.14 (m, 91H), 2.14-1.83 (m, 409H), 1.72-1.33 (m, 400H).

IIIF. Results and Discussion

The synthetic scheme for the semi-fluorinated monomers is as follows. A photochemical [2+2] cycloaddition of 1,5-cyclooctadiene (COD) and maleic anhydride led to 1, which can undergo esterification with 2,2,3,3,4,4,4-heptafluoro-1-butanol to form M1 or react with pentafluoroaniline to generate the imide M2. Monomer M3 was prepared via a [2+2] photocycloaddition reaction between hexafluorobenzene and COD. Both cis- and trans-cyclobutane fused isomers were obtained, with the trans-cyclobutane isomer being the major product. The predominant formation of trans-cyclobutane is consistent with the photocycloaddition of COD and maleic anhydride, suggesting isomerization prior to cycloaddition of the alkene in COD that forms cyclobutane. Compared to the photocycloaddition of maleic anhydride with COD, which has a selectivity of trans/cis>99/1, the lower selectivity for hexafluorobenzene (trans/cis=93/7) could be attributed to a higher reactivity of hexafluorobenzene, according to the reactivity-selectivity principle. The similar polarity of the cis- and trans-cyclobutane products makes separation by column chromatography inefficient. To help the purification of M3, the mixture of isomers was subjected to ring-opening metathesis polymerization (ROMP) to form a polymer that contains both cis- and trans-cyclobutanes. The ring strain energy of the trans-cyclobutane fused cyclooctene is 5 kcal/mol lower than its cis analogue, thus only the polymer of the trans-cyclobutane monomer can depolymerize to form the monomer. Indeed, subjecting the polymer that contains both isomers of cyclobutane to a depolymerization condition (1 mol % Grubbs 2nd-generation catalyst (G2), [olefin]=0.1 M in $CHCl_3$, at 50° C. for 2 h) yielded a mixture of trans-cyclobutane isomer M3 (without its cis analogue) and oligomers, from which M3 was conveniently isolated. It is inconvenient to grow single crystal from M3 since it is a liquid at room temperature. Therefore, epoxidizing M3 to obtain the compound 2 was performed as compound 2 retains the stereochemistry of M3 and is solid at room temperature. X-ray crystallography of the epoxide 2 confirmed the trans-cyclobutane moiety in M3.

Monomers M1, M2, and M3 were polymerized in the presence of G2 at monomer concentrations of >2 M at room temperature. High molecular weight polymers ($M_n$>100 kDa) were obtained with broad dispersity (Đ>1.4) (Table 5). The relatively high dispersity values obtained here were also observed in the ROMP of other low strain monomers using G2. The thermal properties of polymers P1, P2 and P3 were evaluated via thermogravimetric analysis (TGA) and differential scanning calorimetry (DSC). The TGA results showed that P1 and P2 have high thermal stability with $T_d$=335° C. and 395° C. respectively; P3, however, showed a much broader, multi-step thermal decomposition with a lower decomposition temperature of 298° C. The DSC curves revealed that all three polymers are amorphous, as each polymer showed only a glass transition temperature ($T_g$) with no melting temperature. The polymers showed a wide range of $T_g$s: P1 with the more flexible heptafluorobutyl ester side chains showed the lowest $T_g$ of −2° C. while the highest $T_g$ (88° C.) was observed for P2, which possesses a rigid pentafluorophenyl imide substituent. P3, which contains a fluorinated ladderane had a moderate $T_g$ of ~13° C. Additionally, the DSC curve of P3 showed a large exothermic peak with an onset at ~155° C., possibly due to side reactions that cause crosslinking. Compared to its non-fluorinated counterpart P1-NF, which has a $T_g$ of about −31°

C., P1 showed a ~29° C. increase in $T_g$; a similar effect has been previously observed in the comparison between poly (butyl acrylate) and poly(2,2,3,3,4,4,4-heptafluorobutyl acrylate), the $T_g$s of which are −50° C. and −18° C., respectively. P2 showed the opposite behaviour compared to P2-NF, with a decrease in $T_g$ of ~12° C. This is similar to what has been observed for ROMP polymers of N-pentafluorophenyl norbornene-5,6-carboximide ($T_g$=171° C.) as compared to its non-fluorinated counterpart ($T_g$=222° C.), albeit to a lesser magnitude. The wide range of thermal properties obtained herein again highlight the ease with which the thermomechanical properties of the tCBCO polymers can be tuned by simply varying the functional groups attached to cyclobutane.

TABLE 5

Molecular weight information and thermal properties of polymers

| Entry | $M_n$ (kDa)[a] | Đ[b] | $T_d$ (° C.)[c] | $T_g$ (° C.)[d] |
|---|---|---|---|---|
| P1 | 276 | 1.42 | 335 | −2 |
| P2 | 147 | 1.75 | 395 | 88 |
| P3 | 108.3 | 1.64 | 298 | 13 |
| P1-NF | 66.9 | 3.74 | 370 | −31 |
| P2-NF | 105.8 | 1.81 | 409 | 100 |

[a]$M_n$ is the number average molecular weight measured using gel permeation chromatography (GPC) with THF as the eluent, calculated based on a polystyrene standard. [b]Đ is the dispersity ($M_w/M_n$) as determined by GPC. $T_d$ is the temperature at which the polymer experiences 5% weight loss as measured using thermogravimetric analysis. [d]$T_g$ is the glass transition temperature as obtained using differential scanning calorimetry.

The depolymerization of P1, P2 and P3 were studied at a range of concentrations ($[olefin]_o$=25 mM, 50 mM, 100 mM, 200 mM, and 400 mM). The polymer solutions in chloroform were stirred with 1 mol % or 2 mol % G2 at room temperature for ~16 h, which is sufficient for the depolymerization to reach the thermodynamic equilibrium. GPC traces of the depolymerized polymers showed the disappearance of the polymer peak and the appearance of a new peak corresponding to the monomer at longer retention times, along with a small broad peak corresponding to a small amount of residual cyclic oligomers. The extent of depolymerization was calculated by integrating the peaks corresponding to the olefinic protons that correspond to the monomers and the polymer/oligomers in the $^{1}$H NMR spectra. At [olefin] s 50 mM, Pt, P2 and P3 all reached at least 90% depolymerization. At higher concentrations, the extent of depolymerization showed a trend of P1>P3>P2. For example, at [olefin]=400 mM, P1 could be depolymerized to 87% while P2 and P3 to 34% and 61%, respectively. An additional fused ring attached to the cyclobutane can raise the ceiling temperature and inhibit depolymerization and demonstrate the possibility of tuning the thermodynamics of depolymerization through substituent effect.

To evaluate the hydrophobicity of the semi-fluorinated polymers, films of P1, P2, and P3 were prepared on glass slides and their static water contact angles were measured. Both P1 (97.4°) and P2 (91.6°) showed higher contact angles than their non-fluorinated counterparts P1-NF (89.7°) and P2-NF (73.1°), respectively. As shown in FIG. 6 all three semi-fluorinated polymers P1, P2 and P3 showed hydrophobicity with contact angles over 90°, with P1 having the highest contact angle (97.4°), followed by P3 (94.7°) and P2 (91.6°). This trend is consistent with the fluorine content in these polymers: 45 wt. % in P1, 26 wt. % in P2 and 39 wt. % in P3. Angle-resolved X-ray photoelectron spectroscopy (XPS) of polymers with semi-fluorinated side chains has previously shown that fluorinated side chains preferentially orient towards the polymer surface, thus resulting in higher fluorine content at the polymer surface than in the bulk. The preferential orientation of fluorinated groups at the surface positively correlated with the mass fraction of fluorine; fluorine content as a fraction of total surface atoms was also shown to increase with the total mass fraction of fluorine atoms in the polymer, which is correlated with the water contact angle of the polymer. It is likely that such surface orientation effects also contribute to the trend in water contact angles shown.

The hydrophobicity of the semi-fluorinated polymers was applied during synthesis of an amphiphilic block copolymer. Living ROMP of trans-cyclooctene was used to prepare a diblock copolymer P1-b-P4, by sequentially polymerizing E-M1 and a PEG functionalized monomer E-M4. The presence of two incompatible blocks, i.e., a hydrophobic fluorinated block and a hydrophilic PEG block, enables the self-assembly of the block copolymer into micellar structures in an appropriate solvent. To evaluate the solution self-assembly of P1-b-P4, the polymer was first dissolved in THF at a concentration of 10 mg/mL, and to this solution deionized water was slowly added. Dynamic light scattering measurement of the aqueous solution showed a particle size of ~88 nm with polydispersity of 0.279, indicating the successful self-assembly of the block copolymer into a micellar structure.

Post-polymerization functionalization of the pentafluorophenyl imide functionalized polymer P2 was performed using a nucleophilic aromatic substitution ($S_NAr$) of the para-fluoro atom in the pentafluorophenyl unit with an aromatic thiol. The mild conditions, quantitative conversion, and regiospecific substitution at the para-fluoro position together make this reaction particularly useful for post-polymerization functionalization. Thiophenol (1.05 eq. with respect to the p-fluoro atoms in P2) was employed as the nucleophile while an excess of $K_2CO_3$ (1.5 eq.) was added as the base, and the reaction was carried out in 2-butanone at 80° C. Quantitative substitution of the para-fluoro atoms and formation of P2-SPh was observed from the $^{1}$F NMR spectra, indicated by the disappearance of the peak corresponding to the para-fluoro atom in P2 at −152.12 ppm and a downfield shift of the m-fluoro peak from P2 to P2-SPh by ~29 ppm. The GPC traces did not show any significant changes in the molecular weight distribution, while only a slight increase in the molecular weight was observed ($M_n$ measured to be 98.6 kDa for P2 and 103.2 kDa for P2-SPh). The measured molecular weight for P2-SPh is lower than the expected molecular weight (122.6 kDa) assuming 100% substitution. Since the molecular weights were obtained by measuring the hydrodynamic sizes and comparing them to a polystyrene standard, it is likely that the substitution reaction only slightly increased the hydrodynamic radius of P2 despite increasing its actual molecular weight by ~24.3%. As a result, only a minor change in $M_n$ was observed. These effects on the molecular weight and dispersity are similar to those observed for the substitution of poly(2,3,4,5,6-pentafluorobenzyl acrylate) with thiophenol.

Fluorinated polymers pose a significant challenge to closed-loop recycling: Most post-consumer fluorinated polymer waste ends up in landfills, while the persistence of these materials along with the hazards caused by fluorinated small molecules has led to rising concerns about the disposal of such waste. The semi-fluorinated polymers, described above, can undergo CRM under ambient conditions. Depolymerization at over 90% conversion in the presence of ruthenium-based catalysts at room temperature while the modular nature of the tCBCO scaffold has been utilized to incorporate diverse thermomechanical properties. The materials show hydrophobicity, with water contact angles as high as 97.4°, and the hydrophobicity has been further exploited as an amphiphilic diblock copolymer that can form self-assembled micellar structures. The depolymerizable amphiphilic polymers demonstrated here can be used in applications such as antifouling materials and controlled small-molecule release. Post-polymerization functionalization of a pentafluorophenyl imide functionalized polymer, was demonstrated, as a strategy to introduce an additional degree of versatility and functionality, which can be used to prepare complex polymer topologies including star polymers, graft copolymers, and polymer networks. Through the materials developed here, we have expanded the concept of CRM into the domain of fluorinated materials, where such developments were limited to highly energy intensive processes and a small number of materials. We envision that the versatility of this system will enable further incorporation of chemical recyclable polymers into areas where it has been hitherto lacking, including elastomers, thermosets, and fibre-reinforced polymer composites.

What is claimed is:

1. A polymer formed from a plurality of monomers via ring-opening metathesis polymerization, the polymer being capable of depolymerization thereafter through ring-closing metathesis, wherein the monomers of the plurality of monomers comprise the structure according to E-M1:

E-M1

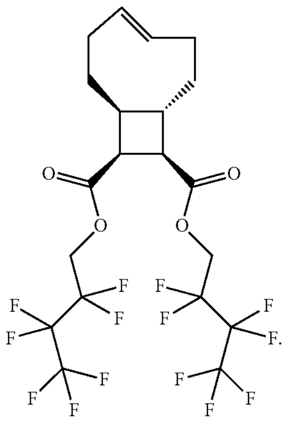

.

2. The polymer of claim 1, wherein the fluorinated functionality of each of the E-M1 in the plurality of monomers is maintained in the polymer.

3. A method of forming a chemically recyclable to monomers polymer, the method comprising:

providing a plurality of monomers comprising the structure according to E-M1:

E-M1

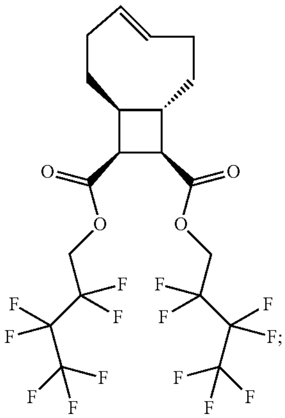

;

and performing ring-opening metathesis polymerization using at least the plurality of monomers, a catalyst as an initiator, a weakly coordinating ligand, and a coordinating solvent to thereby form the chemically recyclable to monomers, polymer.

4. The method of claim 3, wherein an initial concentration of the plurality of monomers is at least 0.010 M.

5. The method of claim 3, wherein the catalyst as an initiator comprises a ruthenium-based catalyst.

6. The method of claim 3, wherein the weakly coordinating ligand comprises triphenylphosphine, $PPh_3$.

7. The method of claim 3, wherein the coordinating solvent comprises tetrahydroguran.

8. The method of claim 4, further comprising depolymerizing the formed chemically recyclable to monomers, polymer, wherein the resulting plurality of monomers comprises a plurality of cycloalkene-fused ring monomers in the lower energy state.

* * * * *